(12) United States Patent
Reiner

(10) Patent No.: US 8,538,776 B2
(45) Date of Patent: Sep. 17, 2013

(54) METHOD AND APPARATUS OF PROVIDING A RADIATION SCORECARD

(76) Inventor: Bruce Reiner, Berlin, MD (US)

( * ) Notice: Subject to any disclaimer, the term of this patent is extended or adjusted under 35 U.S.C. 154(b) by 1255 days.

(21) Appl. No.: 11/976,518

(22) Filed: Oct. 25, 2007

(65) Prior Publication Data

US 2008/0103834 A1    May 1, 2008

Related U.S. Application Data

(60) Provisional application No. 60/854,104, filed on Oct. 25, 2006, provisional application No. 60/960,971, filed on Oct. 23, 2007.

(51) Int. Cl.
*G06Q 50/00* (2012.01)

(52) U.S. Cl.
USPC ............... 705/3; 705/2; 600/300; 348/62

(58) Field of Classification Search
USPC ....................................... 705/2–3
See application file for complete search history.

(56) References Cited

U.S. PATENT DOCUMENTS

| | | | |
|---|---|---|---|
| 5,173,609 A | 12/1992 | Lacoste et al. | |
| 5,511,549 A | 4/1996 | Legg et al. | |
| 5,513,101 A | 4/1996 | Pinsky et al. | |
| 5,621,779 A | 4/1997 | Hughes et al. | |
| 5,655,084 A | 8/1997 | Pinsky et al. | |
| 5,844,241 A * | 12/1998 | Liu et al. ................ | 250/363.04 |
| 5,905,262 A * | 5/1999 | Spanswick ............... | 250/368 |
| 6,058,322 A | 5/2000 | Nishikawa et al. | |
| 6,200,025 B1 | 3/2001 | Rich | |
| 6,222,544 B1 | 4/2001 | Tarr et al. | |
| 6,373,972 B1 | 4/2002 | Nonomura | |
| 6,422,751 B1 * | 7/2002 | Aufrichtig et al. ........... | 378/207 |
| 6,463,181 B2 | 10/2002 | Duarte | |
| 6,487,513 B1 | 11/2002 | Eastvold et al. | |
| 6,628,201 B2 | 9/2003 | Cho et al. | |
| 6,717,154 B2 | 4/2004 | Black et al. | |
| 6,728,662 B2 | 4/2004 | Frost et al. | |
| 6,785,410 B2 | 8/2004 | Vining et al. | |
| 6,790,178 B1 | 9/2004 | Mault et al. | |
| 6,891,476 B2 | 5/2005 | Kitaguchi et al. | |
| 6,919,556 B1 | 7/2005 | Laurence | |

(Continued)

OTHER PUBLICATIONS

Donnelly, Lane F., "Minimizing Ratiation Dose for Pediatric Body Applications of Single-Detector Helical CT", Aug. 2, 2000, American Journal of Roetgenology, 1-13.*

(Continued)

*Primary Examiner* — Sind Phongsvirajati
(74) *Attorney, Agent, or Firm* — Jean C. Edwards; Edwards Neils PLLC

(57) ABSTRACT

The present invention relates to a method to measure, record, analyze, and report cumulative radiation exposure to the patient population and provide automated feedback and recommendations to ordering clinicians and consultant radiologists. The data provided from this "radiation scorecard" would in turn be automatically recorded into a centralized data repository (radiation database), which would be independent to the acquisition site, technology employed, and individual end-user. Retrospective analysis can also be performed using a set of pre-defined scorecard data points tied to the individual patient's historical medical imaging database, thereby allowing for comprehensive (both retrospective and prospective) medical radiation exposure quantitative analysis. Patient safety can be improved by a combination of radiation dose reduction, exposure optimization, rigorous equipment quality control (QC), education and training of medical imaging professionals, and integration with computerized physician order entry (CPOE).

47 Claims, 6 Drawing Sheets

(56) References Cited

U.S. PATENT DOCUMENTS

| | | | |
|---|---|---|---|
| 7,065,235 B2* | 6/2006 | Dewaele | 382/132 |
| 7,084,410 B2 | 8/2006 | Beloussov et al. | |
| 7,171,252 B1 | 1/2007 | Scarantino et al. | |
| 7,205,544 B2 | 4/2007 | Bushberg | |
| 7,206,789 B2 | 4/2007 | Hurmiz et al. | |
| 7,254,643 B1 | 8/2007 | Peters, Jr. et al. | |
| 7,261,690 B2 | 8/2007 | Teller et al. | |
| 7,272,530 B2 | 9/2007 | Hsiung et al. | |
| 2002/0027973 A1* | 3/2002 | Spaak | 378/95 |
| 2002/0131552 A1* | 9/2002 | Nishizawa et al. | 378/65 |
| 2003/0074228 A1 | 4/2003 | Walsh | |
| 2005/0027196 A1 | 2/2005 | Fitzgerald | |
| 2005/0111621 A1* | 5/2005 | Riker et al. | 378/65 |
| 2005/0203775 A1* | 9/2005 | Chesbrough | 705/2 |
| 2005/0209888 A1 | 9/2005 | Oowaki et al. | |
| 2005/0256743 A1 | 11/2005 | Dale | |
| 2006/0017009 A1 | 1/2006 | Rink et al. | |
| 2006/0085223 A1 | 4/2006 | Anderson et al. | |
| 2006/0274145 A1 | 12/2006 | Reiner | |
| 2007/0162311 A1 | 7/2007 | Gentles | |

OTHER PUBLICATIONS

"Assessing Dose of the Representative Person for the Purpose of Radiation Protection of the Public", Annals of the ICRP, Sep. 2006, pp. vii-62, v. 36, i. 3, Elsevier Ltd.

* cited by examiner

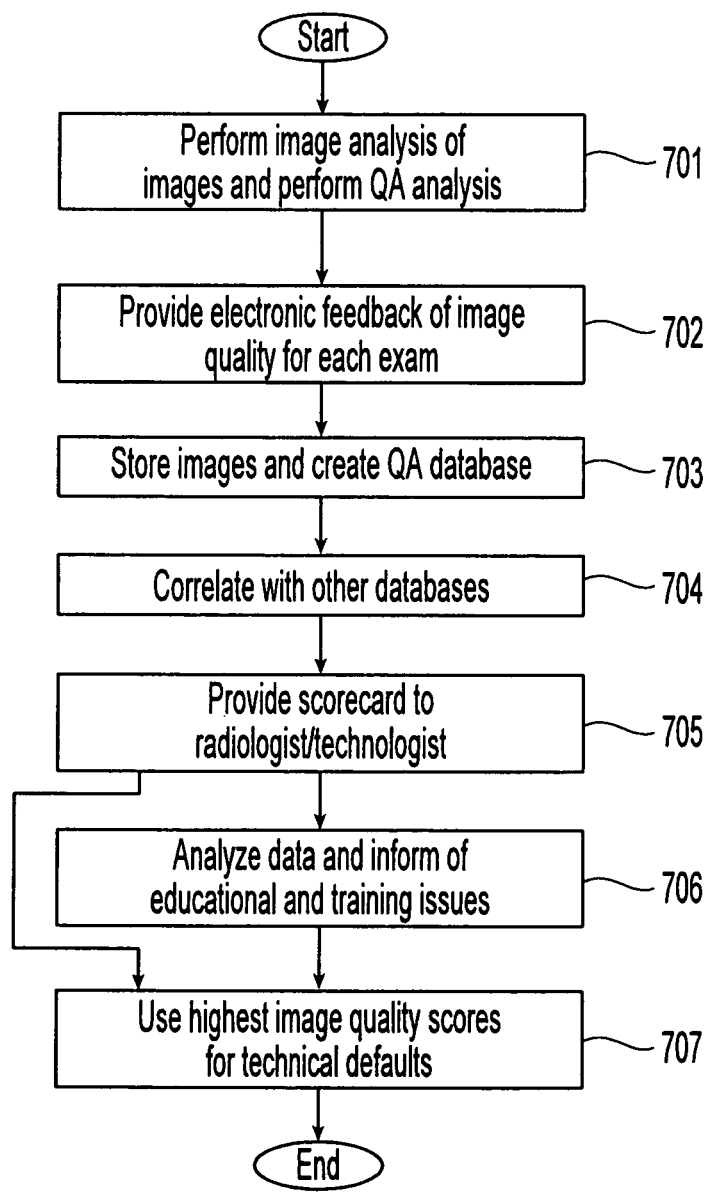

METHOD AND APPARATUS OF PROVIDING A RADIATION SCORECARD

CROSS-REFERENCE TO RELATED APPLICATIONS

The present invention claims priority from U.S. Provisional Patent Application No. 60/854,104, filed Oct. 25, 2006, and U.S. Provisional Patent Application 60/960,971, filed Oct. 23, 2007, the contents of which are herein incorporated by reference in their entirety.

BACKGROUND OF THE INVENTION

1. Field of the Invention

The present invention relates to a radiation scorecard which measures, records, analyzes, and reports cumulative radiation exposure to the patient population and provides automated feedback and recommendations to ordering clinicians and consultant radiologists and technologists. The data provided from this "radiation scorecard" would in turn be automatically recorded into a centralized data repository (radiation database), which would be independent to the acquisition site, technology employed, and individual end user.

2. Description of the Related Art

To date, medical imaging radiation monitoring is largely focused on occupational exposure for healthcare workers (e.g., technologists, radiologists, clinicians), with minimal attention paid to the patient population. While guidelines for radiation exposure exist for all imaging modalities producing ionizing radiation, these are commonly referred to only in problematic situations (e.g., pregnant female).

In its current form, diagnostic medical imaging procedures can expose the patient population to radiation in several different ways including external fixed sources (e.g., radiography or mammography), external moving source (e.g., computed tomography), or internal source (e.g., injected radionuclides). Other medical imaging procedures which deliver ionizing radiation to the patient include general radiography, fluoroscopy, interventional fluorography and angiography. Each different procedure had its own unique set of data points that must be recorded and analyzed, in order to calculate the radiation exposure associated with that event.

In order to compare doses from these different types of imaging procedures, an effective dose must be calculated, which is calculated as the average dose absorbed by body organs and tissues. This effective dose provides a generic equivalent in determining relative radiation risk between different exams but is not specific to the individual patient. In order to accurately track patient-specific radiation dose exposures for a given exam, each individual patient's profile (e.g., body habitus), should be taken into account for accurate quantification of the generic effective dose relative the individual patient—but this is currently not performed.

In the current medical environment, these radiation data points for the different medical procedures are not routinely collected or analyzed within diagnostic medical imaging. In fact, little if any attention is currently paid to radiation dose exposures outside of the pediatric patient population and those occupations routinely exposed to ionizing radiation in the workplace. While radiation dose exposures are calculated for therapeutic applications (e.g., cancer treatment), these are often quantified in isolation, and do not take into account the myriad of radiation exposures encountered with diagnostic imaging studies which are frequent and repetitive within the oncology patient population.

Further, there is no central repository of patient data from which cumulative radiation dose exposure can be calculated, nor is there a feedback mechanism to provide information and recommendations to various stakeholders, such as clinicians, radiologists, technologists, administrators and patients.

Accordingly, a comprehensive method and apparatus of measuring radiation exposure and providing automated feedback to stakeholders is desired.

SUMMARY OF THE INVENTION

The present invention relates to a prospective, longitudinal technology that would measure, record, analyze, and report cumulative radiation exposure to the patient population and provide automated feedback and recommendations to ordering clinicians and consultant radiologists. The data provided from this "radiation scorecard" would in turn be automatically recorded into a centralized data repository (radiation database), which would be independent to the acquisition site, technology employed, and individual end-user.

In addition to prospective radiation exposure data collection, retrospective analysis can also be performed using a set of pre-defined scorecard data points tied to the individual patient's historical medical imaging database, thereby allowing for comprehensive (both retrospective and prospective) medical radiation exposure quantitative analysis. For those patients who have undergone (or are currently undergoing) therapeutic medical procedures using ionizing radiation (e.g., radiation therapy for cancer treatment), the corresponding radiation data from these therapeutic procedures would also be incorporated into the Radiation Scorecard, thereby providing cumulative radiation data from all medical procedures (both diagnostic and therapeutic).

While environmental radiation exposure is difficult to accurately quantify (in the absence of documented data points), prospective environmental radiation exposure can be integrated into the Radiation Scorecard by means of external or internal (i.e., implantable) radiation measuring devices that are intimately tied to the patient. By providing this ancillary record of non-medical radiation exposure, an accurate and reproducible methodology would exist to record, track, and analyze all components of radiation each individual patient would be exposed to during their lifetime. This latter record takes on greater importance in the current environment where radiation exposure related to nuclear weapons (e.g., dirty bombs) has become a harsh reality.

The automated information gleaned from this comprehensive Radiation Scorecard would in turn be used to improve patient safety by a combination of radiation dose reduction, exposure optimization, rigorous equipment quality control (QC), education and training of medical imaging professionals, and integration with computerized physician order entry (CPOE). This data could also be used in the development of new technologies and aimed at reducing environmental, occupational, and medical radiation dose exposures; as well as for medical treatments for radiation-induced disease.

In addition, the comprehensive anonymized meta-data from large patient populations can be used to track individual risk factors associated with iatrogenic complications (e.g., radiation carcinogenesis). This takes on greater importance with new breakthroughs in the human genome, which allow for an individual patient's genomic profile to be correlated with meta-data from the cumulative database to identify each individual patient's radiation profile (which would include a number of quantifiable measures including radiation carcinogenesis risk, tumor response to radiation therapy, and potential for radiation-induced genetic mutations).

Calculation of the effective dose (measured in milliSievert, (mSv)) for each individual diagnostic medical imaging study is possible by assigning sensitive organ "weighting factors", in order to normalize the radiation exposure to the whole body. This outcome measure provides an estimate of a uniformly irradiated whole body dose, which in turn is adjusted according to each individual patient's profile. The specific data points recorded, tracked, and analyzed within the Radiation Scorecard would include peak skin entrance dose, critical organ dose, CTDI, MIRD, and effective dose.

The foregoing summary has outlined some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 6 is a flow chart of an image analysis procedure to achieve a radiologist's and technologist's scorecard, according to one embodiment consistent with the present invention.

DESCRIPTION OF THE INVENTION

Figure 1:
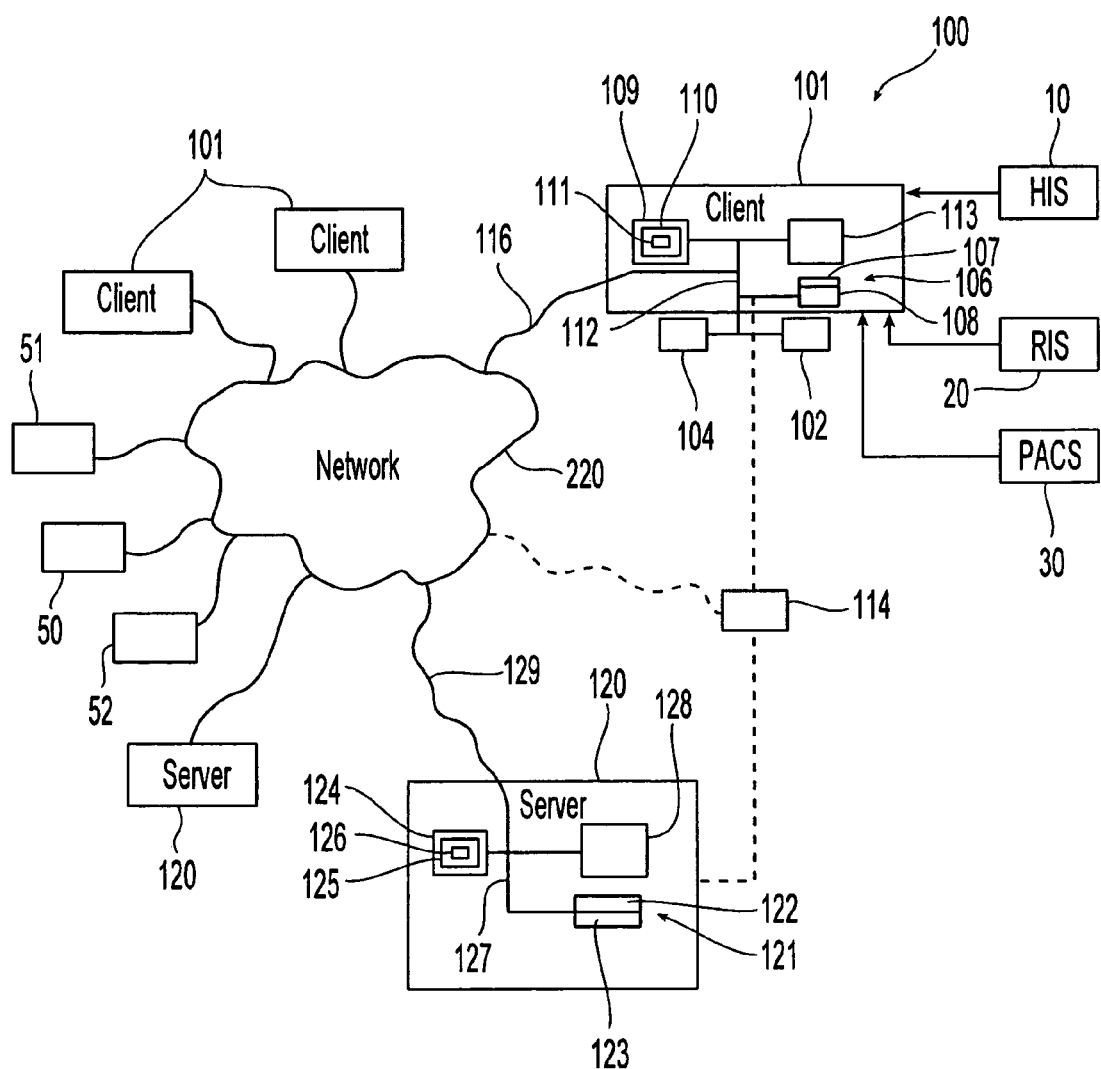
FIG. 1 is a schematic diagram of the apparatus used in one embodiment consistent with the present invention.

According to one embodiment of the medical (radiological) system illustrated in FIG. 1, a system 100 of the invention is designed to interface with existing information systems such as a Hospital Information System (HIS) 10, a Radiology Information System (RIS) 20, and a Picture Archiving and Communication System (PACS) 30, a radiological or other imaging system 50, among other systems. According to one embodiment of the invention, the system 100 may be configured to conform with the relevant standards, such as the Digital Imaging and Communications in Medicine (DICOM) standard, DICOM Structured Reporting (SR) standard, the Radiological Society of North America's Integrating the Healthcare Enterprise (IHE) initiative, and/or other standards.

According to one embodiment of the invention, bi-directional communications between the electronic consultation system 100 and the information systems, such as the HIS 10, RIS 20, and PACS 30, etc., allows the electronic consultation system 100 to retrieve information from these systems, update information therein and provide the desired snapshot templates that are generated by the electronic consultation system 100.

According to one embodiment of the invention, the electronic consultation system 100 may include a client computer 101, such as a PC, which may or may not be interfaced or integrated with the PACS 30. According to one embodiment, the invention includes an imaging display device 102 that is capable of providing high resolution of digital images in 2-D or 3-D, for example. According to another embodiment of the invention, the client computer 101 may include a mobile terminal, such as a mobile computing device, or a mobile data organizer (PDA), that is operated by the user accessing the program remotely from the client computer 101.

According to one embodiment, methods and systems consistent with the invention may be carried out by providing an input mechanism 104 (see FIG. 1), or user selection device, including hot clickable icons etc., or selection buttons, in a menu, dialog box, or a roll-down window of an interface that is provided at the client computer 101. According to one embodiment, commands may be input through a programmable stylus, keyboard, mouse, speech processing system, laser pointer, touch screen, or other input mechanism 104.

According to one embodiment of the invention, the input or selection mechanism 104 may be constituted by a dedicated piece of hardware. Alternatively, the functions of the input or selection mechanism 104 may be executed by code instructions that may be executed on the client processor 106. According to one embodiment, the display unit 102 may display the selection window and a stylus or keyboard for entering a selection, for example.

As described in U.S. patent application Ser. No. 11/512,199, filed Aug. 30, 2006, which is hereby incorporated by reference in its entirety, a multi-functional programmable stylus 104 may be provided to enable input of gestures, symbols, and/or icons through the imaging display device 102. According to one embodiment, other actions may be performed by the multi-functional programmable stylus 104 that are intrinsic to the image display device 102, such as navigation, interpretation, and electronic consultation processes. The actions performed by the multi-functional programmable stylus 104 on the image display device 102 may be superior to actions that are performed using traditional computer keyboard or mouse methods, both within the PACS and Electronic Medical Report (EMR).

The client computer 101 typically includes a processor 106 that operates as a client data processing device. The processor 106 may include a central processing unit (CPU) 107 or parallel processor and an input/output (I/O) interface 108, a memory 109 with a program 110 having a data structure 111, wherein all of the components are connected by a bus 112. Further, the client computer 101 may include an input device or means 104, a display 102, and may also include one or more secondary storage devices 113. The bus 112 may be internal to the client computer 101 and may include an adapter for receiving a keyboard or input device 104 or may include external connections.

According to one embodiment of the invention, the imaging display device 102 may include a high resolution touch screen computer monitor. According to one embodiment of the invention, the imaging display device 102 may be configured to allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104, which may be used to draw the gestures or symbols of the present invention, directly onto the image displaying device 102.

According to one embodiment of the invention, high resolution goggles may be used to provide end users with the ability to review images without the physical constraints of an external computer. For example, a surgeon may wear specialized high resolution goggles to display the cross-sectional radiological image of a brain tumor in 3-D format and may note the gestures on the image, to highlight the pathology in question and to report pertinent characteristics (i.e., anatomic localization, size, etc.), to serve as a guide during surgery. These goggles may be used for image-guided surgery and gesture-based reporting and may serve to provide consultation on pertinent findings during the course of surgery.

According to another embodiment of the invention, an internal medicine physician may use these specialized goggles to review images with embedded gestures or symbols. The images could be downloaded using wireless technology and displayed on the goggles, thereby eliminating the need for a computer screen for image display.

According to one embodiment, the graphical user interface associated with the client computer 101 may be a client application that is written to run on existing computer operating systems. According to one embodiment, the client application may be ported to other personal computer (PC) software, personal digital assistants (PDAs), and cell phones, and any other digital device that has a screen or visual component and appropriate storage capability.

The processor 106 at the client computer 101 may be located internal or external thereto, and may execute a program 110 that is configured to include predetermined operations. The processor 106 may access the memory 109 in which may be stored at least one sequence of code instructions comprising the program 110 and the data structure 111 for performing predetermined operations. The memory 109 and program 110 may be located within the client computer 101 or may be located external thereto.

Note that at times the system of the present invention is described as performing certain functions. However, one of ordinary skill in the art will readily appreciate that the program 110 may be performing the function rather than the entity of the system itself.

According to one embodiment of the invention, the program 110 that runs the electronic consultation method and system may include a separate program code for performing a desired operation or may be a plurality of modules that perform sub-operations of an operation, or may be part of a single module of a larger program 110 providing the operation. The modular construction facilitates adding, deleting, updating and/or amending modules therein and/or features within the modules.

According to one embodiment, the processor 106 may be adapted to access and/or execute a plurality of programs 110 that correspond to a plurality of operations. An operation rendered by the program 110 may include, for example, supporting the user interface, performing data mining functions, performing e-mail applications, etc.

According to one embodiment, the data structure 111 may include a plurality of entries, each entry including at least a first storage area that stores the databases or libraries of gesture symbols, or image files, for example.

According to one embodiment, the storage device 113 may store at least one data file, such as image files, text files, data files, audio, video files, etc., in providing a particular operation. According to one embodiment, the data storage device may include, for example, a database, such as a distributed database that is connected via a network, for example. According to one embodiment, the database may be a computer searchable database. According to one embodiment, the database may be a relational database. According to one embodiment, the storage device 113 may be connected to the server 120 and/or the client computer 101, either directly or through a communication network, such as a LAN or WAN. According to one embodiment, an internal storage device 113, or an external storage device 114 is optional, and data may also be received via a network and directly processed.

According to methods and systems consistent with the present invention, the client computer 101 may be connected to other client computers 101 and/or servers 120, and other medical equipment such as X-ray machines 50 or other imaging equipment. The client computer 101 may also be connected to administration, billing or other systems. According to one embodiment, the connections may be provided via a communication link 116 as a client communication means, using a communication end port specified by an address or a port. According to one embodiment, the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

According to one embodiment, the communication link 116 may be an adapter unit capable of executing various communication protocols in order to establish and maintain communication with the server 120, for example. According to one embodiment, the communication link 116 may be constituted by a specialized piece of hardware or may be realized by a general CPU that executes corresponding program instructions. According to one embodiment, the communication link 116 may be at least partially included in the processor 106 to execute corresponding program instructions.

According to one embodiment consistent with the present invention, if a server 120 is used in a non-distributed environment, the server 120 may include a processor 121 having a CPU 122 or parallel processor, which is a server data processing means, and an I/O interface 123. According to one embodiment, the server 120 may be constituted by a distributed CPU 122, including a plurality of individual processors 121 that are located on one or a plurality of machines. According to one embodiment, the processor 121 of the server 120 may be a general data processing unit. According to another embodiment, the processor 121 may include a data processing unit having large resources (i.e., high processing capabilities and a large memory for storing large amounts of data).

According to one embodiment, the server 120 may include a memory 124 with program 125 having a data structure 126, wherein all of the components may be connected by a bus 127. According to one embodiment, the bus 127 or similar connection line may include external connections, if the server 120 is constituted by a distributed system. According to one embodiment, the server processor 121 may have access to a storage device 128 for storing preferably large numbers of programs for providing various operations to the users.

According to one embodiment, the data structure 126 may include a plurality of entries, each entry including at least a first storage area which stores image files, for example. According to an alternative embodiment, the data structure 126 may include other stored information as one of ordinary skill in the art would appreciate.

According to one embodiment, the server 120 may be a single unit. According to an alternative embodiment, the server 120 may be a distributed system of a plurality of servers 120 or data processing units, and may be shared by multiple users in direct or indirect connection to each other. According to one embodiment, the server 120 may execute at least one server program for a desired operation, which may be needed in serving a request from the client computer 101. According to one embodiment, the communication link 129 from the server 120 may be adapted to communicate with a plurality of clients.

According to one embodiment, the invention may be implemented in software that may be provided in a client and server environments. According to one embodiment, the invention may be implemented in software that can be provided in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

According to one embodiment, in a client-server environment, at least one client computer 101 and at least one server 120 are each connected to a network 220 such as a Local Area Network (LAN), Wide Area Network (WAN), and/or the Internet, over communication links 116, 129. Further, even though the systems HIS 10, RIS 20, PACS 30 (if separate), and imaging equipment 50, are shown as directly connected to the client computer 101, it is known that these systems may be connected to the client over a LAN, WAN, and/or the Internet via communication links. According to one embodiment, interaction with users may be through secure and non-secure internet connectivity. Thus, the steps in the methods consistent with the present invention are carried out at the client computer 101 or at the server 120, or at both. According to one embodiment, the server 120 may be accessible by the client computer 101 over for example, the Internet using a browser application or the like.

According to one embodiment, the client computer 101 may communicate via a wireless service connection. According to one embodiment, the server system 120 may communicate with network/security features, via a wireless server, which connects to, for example, voice recognition. However, one of ordinary skill in the art will appreciate that other systems may be included.

In another embodiment consistent with the present invention, the client computer 101 may be a basic system and the server 120 may include all of the components necessary to support the software platform of the invention. Further, the present client-server system may be arranged such that the client computer 101 may operate independently of the server system 120, but that the server system can be optionally connected. In the former situation, additional modules may be connected to the client computer 101. In another embodiment consistent with the present invention, the client computer 101 and server system 120 may be disposed in one system, rather being separated into two systems.

Although the above physical architecture has been described above as client-side or server-side components, one of ordinary skill in the art will readily appreciate that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations may be carried out in hardware, whereas other of the above processing operations may be carried out using software.

The underlying technology allows for replication to various other sites. Each new site may maintain "state" with its neighbors so that in the event of a catastrophic failure, other server systems can continue to keep the application running, and allow the system to load-balance the application geographically as required.

Further, although aspects of one implementation of the invention are described as being stored in memory, one of ordinary skill in the art will appreciate that all or part of the methods and systems consistent with the present invention may be stored on, or read from, other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the invention, may contain additional or different components.

Accordingly, in one embodiment consistent with the invention, the electronic consultation system 100 and method as used in an exemplary radiology method and system, includes a client computer 101 with image displaying device 102, and an input device 104 which is a programmable stylus. According to one embodiment, the programmable stylus 104 may be used as input mechanism. According to one embodiment, the programmable stylus 104 may be used to perform other tasks that are intrinsic to the image display, navigation, interpretation, and reporting processes of the invention.

Radiation Scorecard

The Radiation Scorecard of the present invention is designed to track, record, and analyze all different forms of radiation including (but not limited to) diagnostic and therapeutic medical procedures, environmental, and occupational exposures. Each of these different radiation sources will have its own unique signature, based on the specific characteristics of the radiation (i.e., energy profile), geographic location, and time/duration of exposure.

The goal of each imaging acquisition is to collect objective and reproducible radiation data, minimize radiation exposure (and its inherent detrimental effects), maximize the quality of the medical data, and provide data mining to improve healthcare outcomes.

The primary strategy is to collect data from the radiation source, which would consist of the medical imaging device (e.g., CT scanner) or therapeutic device (e.g., linear accelerator) 50, for example. Collection strategies are as follows.

a. Radiation Dose Calculations

Prospective calculation of radiation dose exposure is partly dependent upon the specific imaging modality and technology employed. While certain parameters are currently stored within each digital imaging exam's profile (i.e., DICOM header), many of the required data points are easily derived or accessible, but not currently tracked for routine radiation dose calculation.

By defining and integrating these standard, modality-specific radiation metrics into the present invention's Radiation Scorecard, a reproducible mechanism is created to prospectively record and store the requisite data and provide real-time effective dose calculations that can be updated to reflect comprehensive exposure over the patient's lifetime.

A. Digital Radiography

For digital radiography, two major categories of technology exist, differing in the types of detectors utilized and associated data. These include computed radiography (CR) which utilizes passive detectors and direct radiography (DR) which employs active (or integrated) detectors. The integrated detectors have the innate ability to track image acquisition data (including kVp, mAs, collimation, source to image distance (SID), and source to object distance (SOD)). These acquisition data are contained within the DICOM metadata information attached to each image, which can be automatically downloaded by the program 110 into the proposed radiation database 114, for example.

For CR (using passive detectors), most of these DICOM data fields are not automatically recorded and therefore require manual data inputs (from the technologist acquiring the image), in order to assure the corresponding data is routinely captured and stored for radiation dose calculation. This lack of automated acquisition data tracking also exists with the traditional film-screen radiography. However, CR systems do however typically provide an exposure index for each individual image, which provides critical information regarding the effective speed class of the image (contained within the DICOM metadata), which can be used to indirectly calculate radiation dose, in the form of entrance skin exposure. This methodology can also be used to retrospectively estimate radiation dose associated with historical radiographic examinations by using reference data including kVp, mAs, and SID specific to each individual exam type.

Thus, in order to obtain the exposure data for digital radiography, according to one embodiment of the present invention, the radiologist may turn on the client computer 101, which may be a stand-alone PC, or a computer connected to a client workstation known in the radiological field as the PACS workstation 30. In this exemplary embodiment, the client computer 101 may be the PACS 30, and some or all of the present invention, with respect to imaging display device 102, computer memory 109 and program 110 etc., may be contained within the PACS 30 instead of being provided separately.

Thus, according to one embodiment of the present invention, the user may log onto the PACS system 30 once the client computer 101 is operational. Once logged in, the user would bring up the files on the patient in step 301, and would enter and save the specific parameters in step 302, required to accurately estimate the entrance skin dose and effective dose for each patient's particular medical procedure.

For digital radiography, for example, these requisite parameters include acquisition parameters (e.g., kVp, mAs), location and size of beam, geometrical projection (e.g., AP, lateral, oblique), and patient size/girth.

An alternative and system-independent dose calculation can also be derived by using a calibrated dose-area-product (DAP) device installed on the imaging equipment 50 (i.e., x-ray system) within the collimator assembly. The output of this DAP device provides measurements of mGy-cm$^2$, from which surface dose can be estimated by the user or the program 110, with knowledge of the field of view at the surface of the patient (estimated entrance surface dose (mGy)=DAP (mGy-cm$^2$)/skin surface field area (cm$^2$)).

Another system-independent device used for calculating entrance skin dose and effective dose is the use of a point air-ionization chamber measuring air-kerma (kinetic energy released in air) within the DAP device. These dosimeters can be calibrated by the user to provide measurements at a specific distance from the x-ray tube focal spot. If available, the entrance skin dose (mGy) can be directly estimated by the user or the program 110, by adjusting the measured value by the inverse square law, entrance surface dose (mGy)=point dose reported value×(30/SOD)$^2$, where SOD is expressed in units of cm and 30 (cm) is the distance at which the point dosimeter is calibrated in mGy units.

In another embodiment, without knowledge of the exam acquisition parameters or distances employed, entrance skin dose can also be estimated by the user or the program 110 with knowledge of the screen-film speed or exposure index values provided by digital radiography systems (which are contained within the DICOM header), in conjunction with reference values estimated for the specific exam type. Adjustment of the average dose level for a given exam is achieved by the user or the program 110 by taking into account the speed class of the detector and body habitus of the patient. The "matched" reference value (a function of examination, projection, body habitus, detector speed, and patient size/type, e.g., neonate, pediatric, young adult, adult) is the entrance surface dose estimate that is modified by the ratio of the actual measured speed class of the detector ($SC_D$) determined from the DICOM header information to the speed class of the detector used in Reference Value measurements ($SC_{RV}$) to adjust for under or over exposures ($SC_{RV}$ is typically a 400 speed-class value). Thus, the estimated exam Entrance Surface Dose (mGy)=exam RV(mGy)×$SC_D$/$SC_{RV}$.

Once the entrance surface dose is calculated automatically by the program 110, or manually by the user and entered into the PACS system 30 in step 303, the area of irradiation (in terms of critical organs) is determined automatically in step 304 by the program 110. The entrance surface area (ESA, cm$^2$) on the patient is calculated from the image area (IA, cm$^2$) presented on the detector (measurement of image dimensions) corrected for beam convergence to the focal spot, as ESA (cm$^2$)=IA (cm$^2$)×SOD/SID. This area is compared to the field area used for the normalized conversion tables that indicate the fractional organ doses to determine if any adjustments are necessary. Only with large discrepancies between the typical patient entrance surface area and the surface area described in the normalized critical organ dose tables is a correction necessary to either exclude or include critical organs in the radiographic projection.

Then, the effective dose (in mSv) can be automatically calculated by the program 110 as the summation of the product of the entrance surface dose times the fractional organ doses times the critical organ dose weighting factors (publicly available in the recently released ICRP-101 (International Commission on Radiation Protection) documentation.)

Estimates of the fractional critical organ doses for each different type of radiographic exam performed can be obtained by the program 110 from tabular data that exists within the scientific literature that can be prestored in the computer databases 113, 114, for both adult and pediatric patient populations, based upon Monte Carlo simulations.

These fractional values (specific to each individual exam type) can be stored in the computerized database 113, 114 etc. Accordingly, in step 305, the fractional values can be automatically queried by the program 110 at the time of entry of the entrance skin dose into the imaging and information systems databases 113, 114 (e.g., radiology information system (RIS), picture archival and communication system (PACS), and electronic medical record (EMR)), and the effective dose calculated by the program 110 in step 306.

Once the effective dose for each individual exam of each patient is automatically calculated by the program 110 in step 306, the effective dose is downloaded into the patient-specific and universal radiation databases 113, 114 in step 307 and stored by the program 110.

An updated patient-specific cumulative radiation dose estimate can then be automatically derived (i.e., cumulative effective dose estimate) by the program 110 in step 308, for user information, as well as the transfer of dose-related data made, in step 309, to the universal radiation database 114 to use for retrieval for research, new technology development, and meta-data analysis.

B. Mammography

Mammography is somewhat unique in that all significant radiation exposure is confined to the breast. Mean glandular dose is calculated based upon the estimate of the glandular/adipose tissue fraction, compressed breast thickness, and acquisition parameters (kVp, mAs, target/filter, tube output).

In some digital mammography systems, an estimate of the mean glandular dose is provided with the DICOM metadata, which if validated, can be used in lieu of the calculated entrance surface dose. Since the mean glandular dose is directly associated with radiation carcinogenesis, these values are reported and accumulated for each beast independently.

The corresponding effective dose is estimated by the program 110 in step 306 using the critical organ weighting factor of breast tissue, which is 0.12 mSv/mGy. The formula for calculating the effective dose=mean glandular breast dose (mGy)×0.12 mSv/mGy). For an individual mammography exam, the total effective dose determined by the program 110 is the sum of the individually calculated effective dose estimates for each image acquired. Cumulative dose calculation is critically important for mammography, since guidelines recommend annual screening studies throughout the lifetime of the adult female patient beyond the age of 40.

C. Fluoroscopy

Fluoroscopic procedures present a technical challenge for the calculation of radiation dose exposure due to the dynamic nature of fluoroscopy, the non-stationary x-ray beam, varying techniques resulting from attenuation differences on the changing anatomy being imaged, and the geometrical projections changing with motion over a volume area of the patient. Due to these practical constraints, the only existing way to measure radiation dose levels with fluoroscopy is through the use of a DAP meter and/or point dosimeter, as previously described. While these devices are currently not available in many conventional digital fluoroscopic devices, installation can be easily accomplished, in addition to inclusion of the pertinent data elements into the DICOM image header.

Effective dose estimates in step 306 of certain types of fluoroscopic exams (e.g., upper GI series, or barium enema) can be estimated based upon standard projections, from which an overall surface dose and effective dose can be estimated by the program 110. An additional crude estimate of radiation dose exposure can be derived by the program 110 from the recorded fluoroscopy time, with a general rule of thumb of 2 R per minute of tabletop exposure per mA at 80 kVp.

D. Interventional Radiology/Angiography

Estimating effective doses for interventional angiographic exams is calculated by the program in step 306 using the basic requirement that all systems have built-in DAP and point dose measurement devices, and distance measurements including SID and SOD. Similar to fluoroscopy, interventional exams are dynamic in nature and prone to variability. As a result, the recorded DAP and point dose measurements are often not representative of the actual dose received by the patient. For all systems manufactured after June 2006, this data is available in the DICOM XA IOD (information object descriptor) for each acquisition sequence. Using published data values of absorbed organ dose per entrance surface dose and absorbed organ dose per DAP measurements (separate tables for men and women), the effective dose can be calculated by the program 110 using the calculated estimate of the entrance surface dose. There are two ways to estimate the entrance surface dose; using (1) DAP measurements or using (2) the point dosimetry measurements. To use the DAP method, the entrance surface area (ESA, $cm^2$) on the patient is calculated from the image area (IA, $cm^2$) presented on the detector (measurement of image dimensions) corrected for beam convergence to the focal spot, as ESA ($cm^2$)=IA ($cm^2$)×SOD/SID. The DAP is then divided by the ESA for each sequence to estimate the entrance surface dose to the patient (mGy) for the given projection, as: Entrance surface dose (mGy)=DAP (mGy-$cm^2$)/ESA ($cm^2$). To use the point dose measurement per acquisition sequence, the Entrance surface dose (mGy)= point dose reported value×$(30/SOD)^2$, where SOD is expressed in units of cm and 30 (cm) is the distance at which the point dosimeter is calibrated in mGy units. The effective dose is then estimated in the standard way as previously described E. Computed Tomography Radiation dose calculation for CT in step 306, is largely determined using indirect measurements obtained from plastic phantoms (different sized phantoms used for different anatomic regions). The weighted CT dose index (CTDIw) is a measure in milliGrays (mGy) of the radiation dose measured at the periphery and center of the phantom, using the ratio 1/3 center+2/3 periphery (as a function of kVp and slice thickness). For volumetric CT acquisition with state-of-the art CT scanners, CTDIvol refers to the CTDIw divided by the pitch (which refers to CT table travel per 360 degree rotation of the x-ray tube). Dose Length Product (DLP) is the product of CTDIvol multiplied by the table travel in centimeters.

Software developed by the Imaging Performance Assessment of CT Scanners (ImPACT) group can be used to directly calculate CTDIw, DTDIvol, and DLP using the specific exposure parameters (CT scanner type, kVp, effective mAs, helical pitch).

Modern CT scanners provide post-scan radiation dose information (CTDI and DLP) in the DICOM metadata (described by the CT IOD).

Effective dose in mSv for a CT examination is determined from the DLP values using conversion coefficients, as E(mSv)=$E_{DLP}$×DLP, where $E_{DLP}$ is the anatomy-specific dose coefficient expressing the effective dose normalized to the DLP in the standard CT dose phantom, with units of mSv/(mGy-cm). Coefficient data are adjusted for patient size and patient age to achieve acceptable accuracy.

F. Nuclear Medicine

Unlike other imaging modalities, radiation dose for nuclear medicine is independent of the imaging technology and patient body habitus, and instead totally dependent upon the type and dose of radiopharmaceutical utilized. The Medical Internal Radiation Dosimetry (MIRD) is a well-established methodology for calculating organ specific and whole body radiation dose exposures. By simply computerizing these established look-up tables, radiation dose calculations can be readily determined for all nuclear medicine exams by simply inputting the type and dose of radiopharmaceutical injected as in step 305 of FIG. 2.

Figure 5:
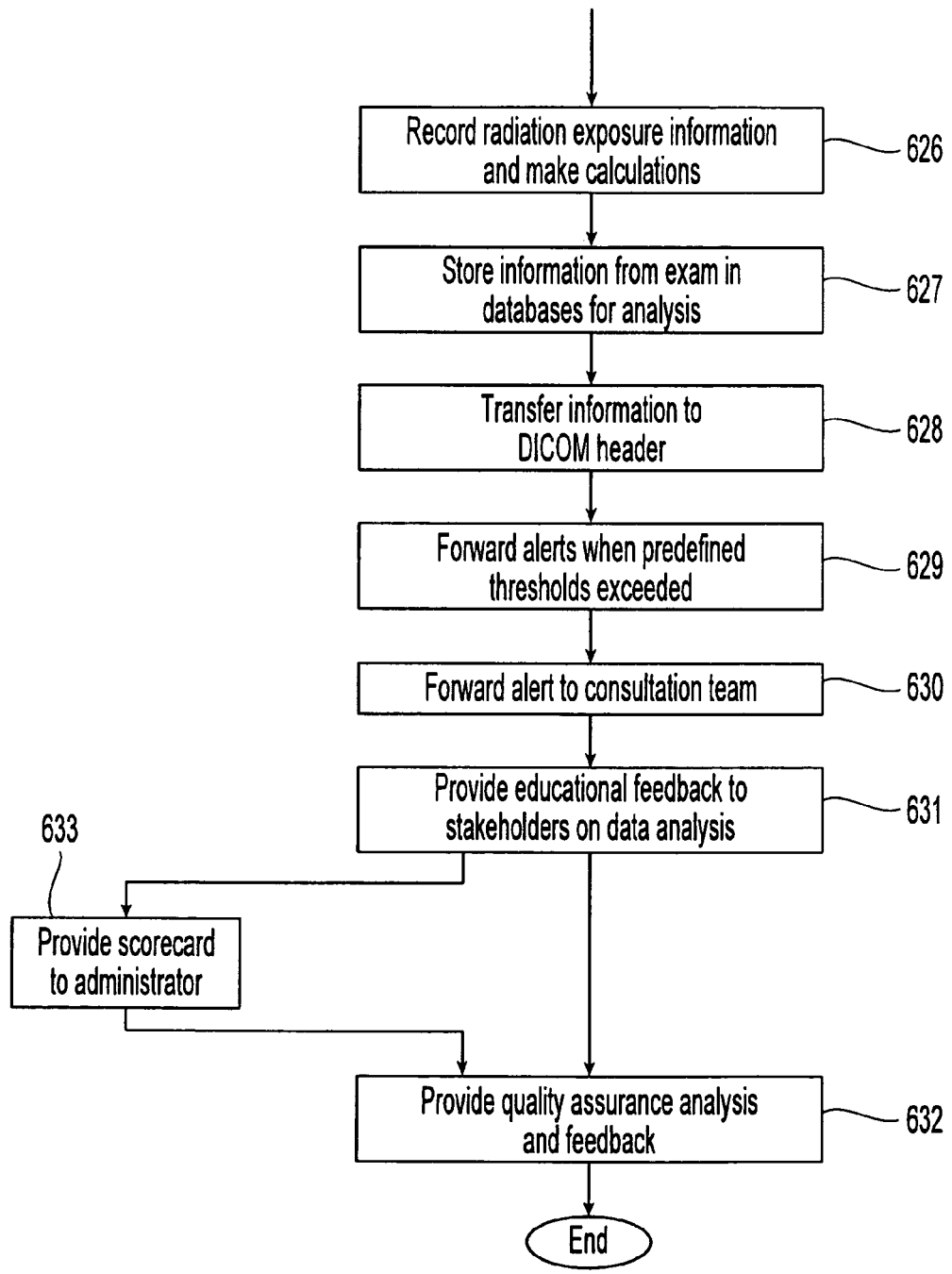
FIG. 5 is a flow chart of how the radiation scorecard is compiled by analysis of the images taken, of how the analysis of the information is performed, the feedback provided to the stakeholders, and how quality assurance performed, according to one embodiment consistent with the present invention.

This radiation exposure data in nuclear medicine may be captured in the DICOM header, and could easily be mandated to accommodate automated dose calculations (see step 628 of FIG. 5).

Figures 2, 4:
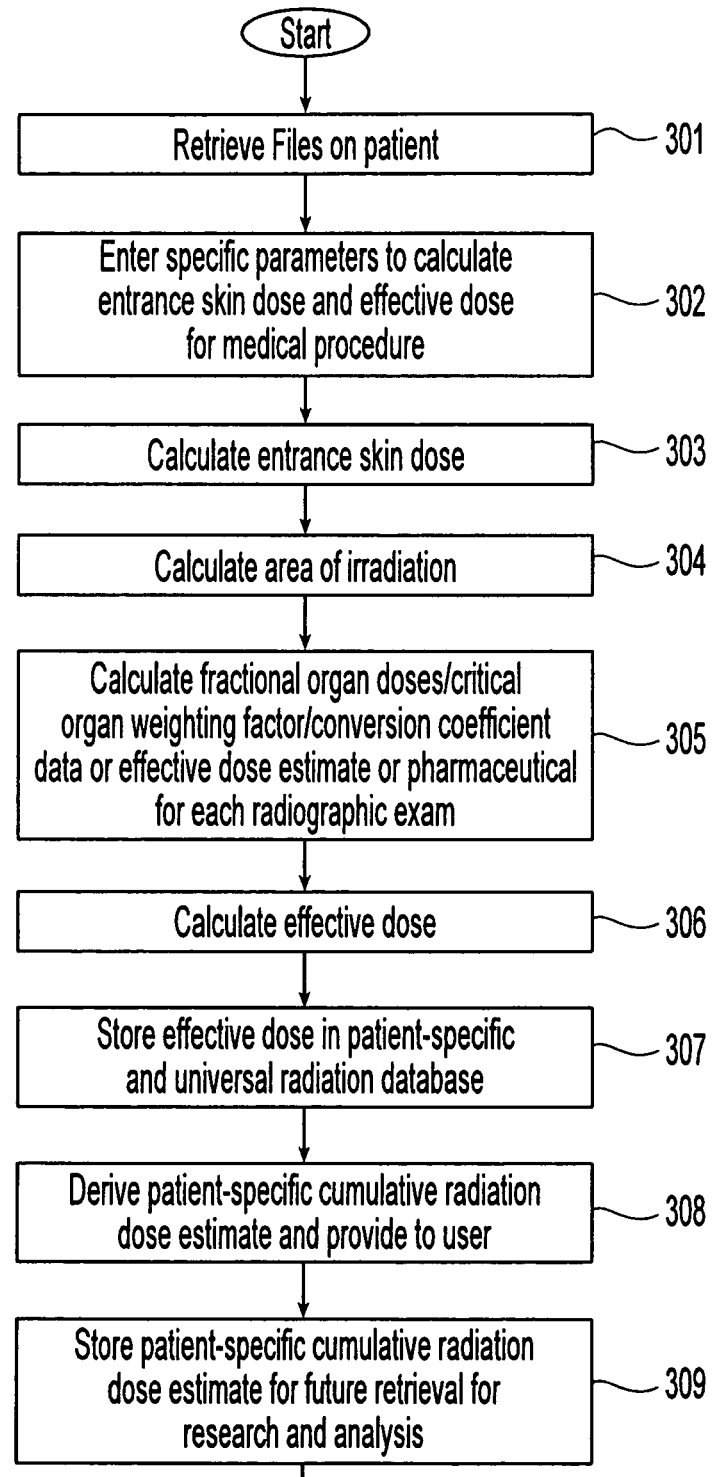
FIG. 2 is a flow chart of how to achieve an effective dose according to one embodiment consistent with the present invention.
FIG. 4 is a flow chart of how a technologist performs an imaging examination and utilizes the radiation scorecard and radiation databases, according to one embodiment consistent with the present invention.

This data can in turn be automatically transferred into medical information technologies (e.g., PACS, EMR) by the program 110, for the purposes of creating centralized local, regional, or national radiation databases 114 (see step 309 of FIG. 2).

b. Radiation Data Collection

Regardless of which technology and methodology is used to calculate radiation dose exposures, these calculated data are automatically downloaded by the program 110 into a series of databases 113, 114, which are accessible to the patient and any designated healthcare providers involved in that patient's medical care. In addition to all prospective dose calculations, retrospective dose exposures can be estimated by the program 110, for example in step 302 (see FIG. 2) using historical data points (depending on accuracy) from the patient's medical records contained within a variety of information systems including the EMR, RIS, and PACS. With the recent advent of digital imaging and data storage, retrievability of pertinent data has become far easier and more complete than in the past with analog imaging and paper-based medical records.

In order to collect objective and reproducible data related to radiation exposure, data may be collected from the radiation source 50 in step 310, which would consist of the medical imaging (e.g., CT scanner) or therapeutic device (e.g., linear accelerator). This data can in turn be automatically transferred into medical information technologies (e.g., PACS, EMR) by the program 110, in step 626 (see FIG. 5), for the purposes of creating the centralized local, regional, or national radiation databases 114, for example. Thus, independent of the imaging modality or technology being used, radiation exposure can be obtained by externally recording all ionizing radiation through an external (or implantable device (e.g., diode)) that would record all radiation exposure to the patient in step 626.

The external radiation data monitoring sources 51 (computerized sensors with microprocessors, for example) can be imbedded within the medical imaging/therapeutic devices 50 or attached to the patient in a number of forms including (but not limited to) jewelry (e.g., bracelet, necklace), implantable computer chips, or physically embedded within clothing, for example.

This external radiation monitoring sources 51 can be directly tied to biometrics technology 52 (see for example, U.S. patent application Ser. No. 11/790,843, filed Apr. 27, 2007, the contents of which are herein incorporated by reference in its entirety) to ensure proper linkage of the radiation data and patient-specific radiation database 113, 114 by the methods described therein. Further, in one embodiment, the patient's identification may be established and authenticated using biometrics directly integrated into the imaging device 50 (i.e., CT scanner), as in step 615 (see FIG. 4) and then all patient-specific radiation data may be simultaneously transferred by the program 110 to the DICOM header (contained within each individual image), RIS, PACS, and EMR, for example, immediately after exam completion in step 628 (see FIG. 5).

The data recorded in step 626 by the radiation monitoring sources 51, may include, for example, the date and time of exposure, the duration of exposure, the amount of the dose, the geographic location (using GPS technology), the anatomic area of exposure, the energy profile of the radiation (each radiation source has its own unique profile), as well as the geographic location (longitude/latitude, altitude) of the exposure, during a given interval.

The radiation monitoring sources 51 can transfer data to the radiation databases 113, 114 in several ways. In one embodiment, scanners/readers 52 can be used, for example, in a hospital, to download information from the radiation monitoring sources 51 and transfer the patient-specific radiation data to the centralized database 113, 114, regionally, nationally, or internationally, at predetermined intervals, using a biometrics tag in the monitoring sources 51, that is specific to the patient.

Alternatively, the patient-specific radiation data can be read by wireless devices 53 and stored locally in computers embedded within everyday appliances (e.g., PDA) 54 at the patient's home or office, or downloaded directly, via the internet, into a centralized database 113, 114. In a home or office situation, the local database in the everyday appliances 54 may be automatically updated each time a new radiation exposure is recorded by the radiation monitoring sources 51. Then the data can be transferred/downloaded by the program 110 from the appliances 54 over the internet, using patient-specific biometrics, into the centralized databases 113, 114 at pre-determined intervals (e.g., daily, weekly, monthly). The databases 113, 114 may be regional, national, and international and would include information from the patient's EMR.

Further, in one embodiment, the program 110 can cross-reference the downloaded and stored information with each individual patient's calendar, to create a time-stamped radiation profile, that could categorize the radiation source in detail.

If, for example, that same patient underwent a mammographic exam, the combined geographic location (e.g., Hospital medical imaging department), radiation profile (ionizing radiation fitting the profile of a screening mammogram), and date/time of exposure, would be recorded by the radiation monitoring device 51 in step 310, recorded, or read and downloaded by the scanner/reader 52, and saved in a radiation database 113, 114.

In one embodiment, the program 110 would receive radiation exposure information for a particular anatomic region/critical organ, and would compare it to a maximize radiation exposure for that anatomic region/organ.

The program 110 can also analyze the relative quantitative differences in simultaneous exposure when the information is downloaded into the databases 113, 114, and a topographical 3-dimensional anatomic map may be created by the program 110 that illustrates the epicenter of maximal radiation exposure (i.e., anatomic region/organ), as well as the relative decay in radiation exposure as one travels in a 3-dimensional fashion away form this point. This would in effect, create a real-time anatomical, temporal, and quantitative map of radiation exposure that could longitudinally track a patient's radiation exposure over time, with an in-depth analysis of whole body, organ specific, and individual points of exposure. This would be of critical importance when excessively high exposure levels are experienced within a specific, highly sensitive anatomic region.

One benefit of the creation of a standardized radiation lexicon is that all data within the Radiation Scorecard and its databases 113, 114 would be independent of differences in the radiation source, technology utilized, and institutional demographics.

While the Radiation Scorecard database 113, 114 is principally designed for tracking medically related radiation data, environmental and occupational radiation exposure is also recorded and analyzed. In the current environment of potential nuclear warfare and terrorism, the Radiation Scorecard also provides a means to define external radiation sources and their associated morbidity and mortality. In a previous section of this document, a number of external (and internal) radiation sensors were described that serve to measure, record, and analyze radiation exposures.

Further, in the case of environmental radiation sources of larger radiation magnitudes, external sensors or monitoring devices 51 can serve to continuously monitor environmental radiation levels and identify any unexplained incremental increases in radiation beyond baseline. These sensors 51 can be distributed in a manner similar to ubiquitous computing and linked as individual nodes on a comprehensive network. The location of each sensor 51 would be established using GPS software and any deviations beyond normal baseline can direct an emergency response and early intervention. By linking these sensors 51 onto a comprehensive network, the epicenter of the radiation exposure can be quickly identified and directionality of the exposure can be immediately established and correlated with environmental factors (e.g., wind speed and direction) to accurately predict extent and direction of contamination. At the same time, individual sensors (internal or external to the individual end-user) can determine sudden changes in radiation exposure to correlate with the external environmental sensors; rapidly identifying those individuals in need of emergent medical care and prophylaxis.

For example, if a person was exposed to excessive radiation exposure due to an occupational or environmental hazard (e.g., radioactive spill, dirty bomb), the extent of whole body exposure, as well as critical organ exposure could be calculated using the method and apparatus of the present invention. The program 110 will utilize the information in the radiation scorecard and databases 113, 114 to identify at-risk areas, direct first responders, and facilitate treatment in the event of large-scale radiation contamination. This same principle can also be used with other environmental catastrophes (e.g., bioterrorism), where external/internal sensors could be used to record exposure to biologic agents and direct rapid response and treatment. This would also apply to radiation exposures associated with therapeutic procedures (e.g., radiation treatment for cancer).

Thus, the Radiation Scorecard is designed to track, record, and analyze all different forms of radiation including (but not limited to) diagnostic and therapeutic medical procedures, environmental, and occupational exposures, for example. Each of these different radiation sources will have its own unique signature, based on the specific characteristics of the radiation (i.e., energy profile), geographic location, and time/duration of exposure.

c. Radiation Scorecard Implementation

Implementation of the Radiation Scorecard of the present invention requires integration of existing standards, which currently exist through a number of societal organizations including American College of Radiology (ACR), American Association of Physicists in Medicine (AAPM), and the Euratom directives.

The data contained within the Radiation Scorecard are collected, analyzed, and stored within information system technology (RIS, PACS, EMR) and the radiation databases 113, 114.

In one exemplary embodiment, the patient presents to the medical imaging department for a new imaging exam, and identification can be established by either using biometrics analysis (integrated directly into the imaging modality) or by using a patient-specific unique identifier in step 612 (see FIG. 4). Once the patient is identified within the database 109, 113, 114, the examination can continue.

The effective dose is calculated using steps 301-309, and the radiation exposure data inherent to the new imaging study is collected in step 626 and downloaded directly by the program 110 into the centralized database(s) 113, 114 in step 627 for future analysis.

The program 110 will then derive standardized information for the Radiation Scorecard from the data collected and stored, so that the imaging study data which is analyzed by the program 110 may be consistent across different patient populations, medical institutions, and imaging technologies. While the comprehensive scorecard information would be consistent and reproducible, individual scorecards can be customized to the unique perspectives and needs of individual stakeholders, as follows:

While the data recorded, tracked, and analyzed within the Radiation Scorecard overlaps to some degree with the QA Scorecards (since both are quality-centric) of copending U.S. patent application Ser. Nos. 11/699,349, 11/699,350, 11/699,344, 11/699,351, 11/699,348, all filed Jan. 30, 2007, the contents of which are herein incorporated by reference in their entirety—the radiation data extends beyond medical applications alone (including both environmental and occupational radiation exposures) and serves as a mechanism for decision support as it relates to patient radiation risk (i.e., safety) and future technology development and use (customized to the patients' unique profile). While the QA Scorecard longitudinally track quality metrics related to the medical imaging chain, the Radiation Scorecard extends throughout all medical and non-medical applications resulting in radiation exposure. By integrating the patient's medical history, genetic profile, and radiation susceptibility the Radiation Scorecard becomes a prospective means to monitor radiation exposure, predict radiation-induced illness, provide prospective feedback on technology utilization (for radiation dose optimization), guide the development of new technologies (e.g., nanotechnology), and treat medical disease (e.g., through new and existing forms of radiation therapy).

A. Clinicians

Clinicians have the important responsibility of exam ordering, which is a complex task that requires assimilation of multiple clinical and imaging data, including (but not limited to) the clinical indication, patient profile, past medical/imaging history, and diagnostic options available.

Figures 3, 4:
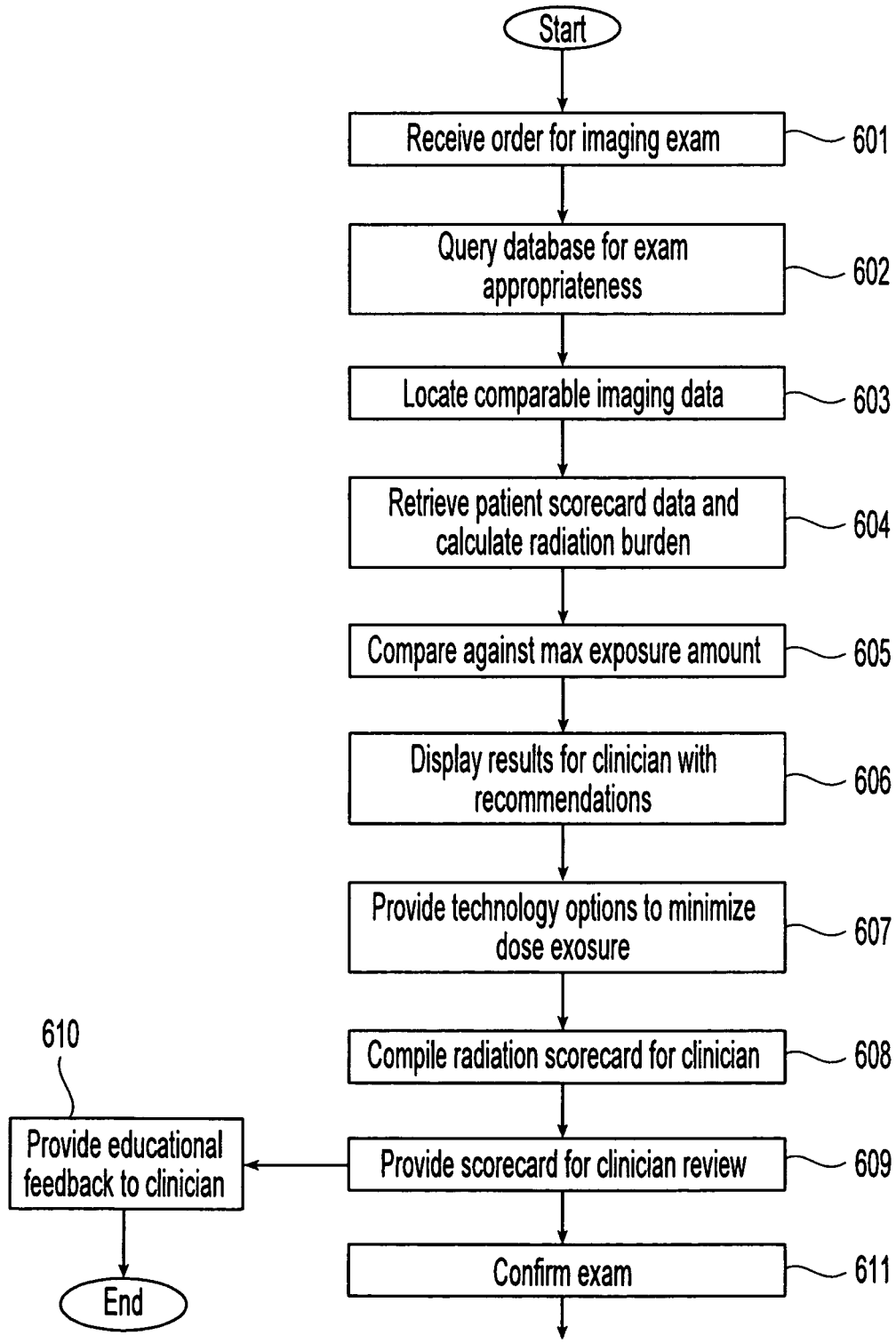
FIG. 3 is a flow chart of how the radiation scorecard is achieved with respect to a clinician's participation, according to one embodiment consistent with the present invention.
Figure 4:
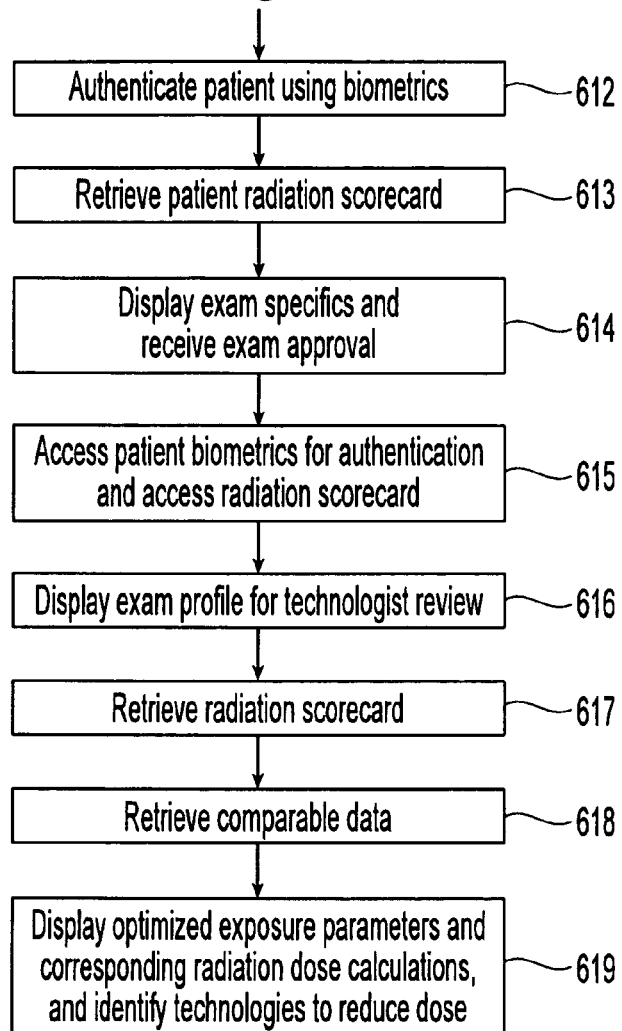

The clinician's ordering history would in turn be recorded by the program 110 in step 601 (see FIG. 3) and entered into a centralized database 113, 114 for analysis with educational feedback as to how imaging exam ordering (and associated radiation dose) compares to the exam ordering of the physician community at large, based on a series of patient and context-specific data. In particular, the databases 113, 114 will include a series of prospective patient and context-specific data as it relates to imaging exam appropriateness criteria, comparative radiation dose exposures (and costs) of different imaging exam options, individualized patient radiation profile, and industry-wide standards, which the program 110 will utilize in its analysis.

At periodic intervals (e.g., every 3 months), the program 110 will perform an analysis of the exam ordering, and the clinical, economic, and patient safety concerns based on the clinical indication and patient profile, and provide this information to the clinician in step 609 in the form of a scorecard or "report card grade". This information can in turn, by analyzed by the program 110, for notifying the user in step 610, of issues where remedial education and training may be necessary, with the goals of improving patient safety and diagnostic efficacy of medical imaging. (See Quality Assurance for Radiology of copending U.S. patent application Ser. No. 11/412,884, filed Apr. 28, 2006, the contents of which are herein incorporated by reference in their entirety, and U.S. patent application Ser. No. 11/699,351). Third-party payers can in turn partially tie physician reimbursement (i.e., Pay for Performance (P4P)) to these objective data contained within the Radiation Scorecard.

B. Radiologists

Radiologists, by training are considered to be defacto experts in the topic of medical imaging radiation and are often deferred to when clinical questions arise as to radiation exposure and patient safety as it relates to ionizing radiation associated with medical imaging. Unfortunately, most radiologists have little if any impact when it comes to the ordering of medical imaging studies. Most imaging departments operate using standardized imaging protocols, which positively impact workflow and operational efficiency, yet has a potentially detrimental effect on the ability to perform dose optimization (which balances the often competing demands for dose reduction and image quality).

By automating radiation dose and medical imaging data collection and analysis as in the present invention, radiologists have the opportunity to become more proactive participants in exam selection, protocol optimization, image processing, image quality analysis, dose reduction, and education and training (clinicians, technologists, and patients). Since radiologists are ultimately responsible for interpretation of medical imaging studies, their input into image quality is essential in the overall Quality Assurance (QA) program.

In the present invention, the program 110 may provide an automated procedure which will perform an image analysis of each image taken by the imaging equipment 50, so that a quality analysis can be automatically derived by the program 110 in step 701 (see FIG. 6), and electronic feedback of image quality provided for each individual exam to the radiologist in step 702. This image quality can be stored by the program in step in the databases 113, 114, and the program 110 can use this information to create an electronic QA database (see step 703) (as part of or separate from the radiation databases 113, 114).

This data can in turn be correlated by the program 110 in step 704, with local, regional, and national reference databases 113, 114 to provide radiologists (individual and groups) with similar report card grades as the clinicians in step 705, which can be updated on a quarterly basis by the program 110 to provide performance feedback. See copending U.S. patent application Ser. No. 11/412,884.

In step 706, this report card/scorecard information can in turn, by analyzed by the program 110 to notify the user of issues where remedial education and training may be necessary, with the goals of improving radiologist or technologist education and training (similarly to that of the clinician above).

In addition, as stated in U.S. patent application Ser. No. 11/699,344, those exams with the highest image quality scores can be identified by the program in step 706, and used by the program 110 as to provide technical defaults for future imaging studies (thereby reducing the inter-exam variability in technique, radiation dose, and image quality).

This data can also be made available to the public, to facilitate continued educational efforts and informed decision-making. A portion of radiologist (professional component) reimbursement can be tied to these performance metrics (P4P) and continued medical education, thereby creating added incentive to become proactive participants in radiation safety.

C. Technologists

As stated in U.S. patent application Ser. No. 11/699,348, when evaluating individual and collective technologist performance, the program 110 takes into account a number of factors which require consideration including (but not limited to) productivity, exam quality, retake/reject analysis, exposure parameters, image processing employed, and patient adverse outcomes.

All the data on these factors, which is collected by the program 110 in step 626, and stored by the program in step 627, and then analyzed accordingly—in some degree contribute to overall patient safety and either directly or indirectly influences radiation dose delivery. Technologists that proactively utilize specialized dose reduction techniques, minimize exam retakes, optimize quality (in terms of imaging, historical, and clinical data), and reduce adverse outcomes will in turn result in improved patient safety and cumulative reduction in radiation exposure.

The program 110 utilizes the radiologist feedback on QA as described above (contained within the QA database 113, 114), to prepare a scorecard or report card for the technologist, which is provided by the program 110 in step 705, in quarterly updates, for example. Thus, the technologists have the opportunity to receive regular updates as to QA limitations and the perceived image quality associated with different technical parameters. Technologists who access this data on a regular basis and demonstrate quality improvement, dose reduction, and improved patient safety measures can be recognized and receive financial incentives and promotional opportunities tied to objective performance review.

D. Administrators

One of the most important challenges facing any hospital or radiology department administrator is optimizing patient safety, which tends to be reactive, rather than proactive. Any adverse patient action generates a thorough review (i.e., root cause analysis), which in turn leads to a series of operational changes to minimize a repeat offense.

With the heightened awareness of radiation safety concerns, more medical imaging department customers (patients, clinicians, and third party payers) are expressing a greater interest in improved patient safety, and clinical outcomes. Medical imaging providers are tasked with responsibility of ensuring equipment quality control, optimizing imaging exam selection, minimizing patient radiation exposure, and optimizing diagnostic accuracy. In order to accomplish these goals, as stated in U.S. patent application Ser. No. 11/699, 350, for example, rigorous QA, QC, and radiation safety standards are required with collection of QA data by the program 110, with continued monitoring, documentation, and analysis by the program 110 of this data in step 632, to ensure established performance metrics are being achieved.

The Radiation Scorecard provides an objective means to record and analyze these data, and provide it to the administrator as a report card in step 633, based on a correlation with the national reference databases 113, 114—providing an objective method of success.

The combination of multiple data points within the Radiation Scorecard provide objective means for analysis at the levels of the individual patient, technologist, technology utilized, department, referring clinician, and peer groups (i.e., institutions) at local, regional, national, and international levels. This provides an administrator with the abilities to not only evaluate performance and adherence to community-wide standards, but also integrate new and existing technologies into workflow to facilitate improved safety and quality measures. The added ability to use this data for education and training purposes (for all stakeholders) (see step 631) creates an added mechanism to incentivize improved measures of performance and provide feedback to outliers. One of the greatest challenges facing administrators is determining "best practice guidelines", determining the optimal balance (between economics, patient safety, and image quality), and integrating disparate technologies. The Radiation Scorecard data provides an effective means to track these parameters (through statistical analysis) in a customized fashion depending upon the unique variables and preferences of each institutional provider.

One example of how technology integration can be positively affected (and driven) by the Radiation Scorecard is as follows.

Imaging provider A is developing a new application (e.g., cardiac CT angiography) for its clinical service population. The administrator overseeing implementation must determine what technology to purchase and how it will be integrated into existing technology (e.g., CT scanner, PACS, EMR).

When obtaining quotes from prospective vendors through an RFP (request for proposal), the administrator creates a spreadsheet for comparative analysis that typically compares economic measures and technical specifications (specs) of the technology. Using national data contained within the Radiation and QA Scorecards (that can be fractionated based in institutional demographics to match the host institution), the administrator can identify how the various vendors' technologies differ in quality, workflow, and radiation metrics.

The administrator can incorporate additional variables into the comprehensive spreadsheet for analysis that take into account these safety and quality variables and create "weighted" measures according to their own list of priorities. In addition, the administrator can identify what specific technology options (e.g., 3-D reconstruction software) and supplemental technologies (e.g., specialized image processing algorithms) that can further improve safety and quality.

By incorporating both input (e.g., technology cost and performance) and output data (e.g., economic incentives tied to quality (P4P), reduced medico-legal liability); the administrator can make an educated and informed decision (i.e., cost-benefit analysis) as to technology selection, integration, and corresponding service deliverables. In the absence of the Radiation (and QA) Scorecard, this decision process is highly subjective and lacks the ability of objective data which can be customized to institutional preferences, existing technology, and expected service deliverables.

E. Patients

The cumulative radiation dose exposure over the lifetime of the patient can produce a substantial risk for carcinogenesis, and this has been shown to be highest in industrialized countries. As preventive medicine takes on greater importance to healthcare strategies, non-invasive medical imaging screening studies (e.g., mammography) play an important role, thereby producing an additive risk for radiation induced morbidity and mortality.

The Radiation Scorecard provides an objective means to quantify this risk, provide education and feedback as to alternative technologies and new imaging applications, and comparative data as to medical imaging providers' overall performance.

By implementation of the Radiation Scorecard all radiation dose exposures (related to medical diagnostic procedures and treatment, occupational, and environmental) are recorded into the master database 113, 114 in step 626. This longitudinal analysis can also provide estimates of previous exposures in step 627 based on the historical data contained within the EMR, PACS, and RIS.

The patient profile is then created by the program 110 in step 201 (see FIG. 2) after consultation with the patient, which can take into a number of variables including (but not limited to) the following:

a) Patient medical problem list (i.e., list of past and current medical problems requiring treatment).

b) Family history c) Patient-specific predisposition to new diseases. (These items are derived from genetic (DNA) analysis of the individual patient to identify the relative risk factors which predispose each individual patient to radiation injury and predisposition to new medical/surgical disease processes.)

d) Patient susceptibility to radiation-induced injury/illness. (Same as c)).

e) Subjective perceptions (of the patient) to radiation, quality, and economics.

f) Estimation of non-medical (environmental and occupational) radiation exposures.

g) Prospective analysis (as it relates to radiation utilization patterns) of practice patterns of primary and secondary caregivers (i.e., primary care physician, medical/surgical consultants).

This comprehensive data is then reviewed in step 202 with the patient and a multi-disciplinary radiation consultation team (which can consist of medical physicist, primary care physician, radiologist, radiologic technologist, information technology (IT) specialist, and geneticist) to create a customized patient profile.

This profile is then used to determine future medical decision-making (e.g., screening and preventative procedures using ionizing radiation), consultative services, direct feedback, and educational programs (see steps 629-631 in FIG. 5).

The multi-disciplinary team creates a prospective program for the patient that includes frequency of updated information, preferred mode of information delivery, quantitative threshold for emergent alerts, automated educational programs (which can be based on new and/or existing technology, recommendations for preventative medicine/screening tests, updates on existing medical conditions) (see steps 629-631).

In addition, the patient can be provided with periodic data tabulations on radiation profiles related to their medical/surgical providers (i.e., their Radiation and QA Scorecard "grades"), different imaging providers, and environmental exposures in step 306 (see FIG. 2).

The ultimate goal is to create an educated patient population which understands the dangers of radiation and can actively participate in their own healthcare decisions (based on their own preferences and perspectives).

At the same time, the centralized database 113, 114 provides a detailed record of patient imaging exams, thereby reducing the potential for unnecessary and repeat medical imaging exams.

Many times patients go from one medical provider to another and in the process have a duplication of services, which can include radiology exams with ionizing radiation. The database 113, 114 would not only identify all radiation exposures but also provide prospective feedback to each provider (e.g., internist, radiologist, technologist) as to what exams have been performed, where they were performed, the technical aspects of the exams performed (e.g., exposure parameters and effective dose), and alternative recommendations to improve radiation exposure (see steps 308, 623, 624, 701 etc.).

F. Physicists

In most community medical imaging facilities, physicists participation in radiation safety is limited to periodic inspection and data collection (on a consulting basis), in order to comply with community standards (e.g., JCAHO, MQSA). This cursory level of involvement satisfies the bare minimum, but does not take advantage of the expertise and specialty training of medical physicists, as it relates to a number of patient-safety radiation concerns such as quality control (QC) and equipment monitoring, dose calibration, and image quality and dose optimization.

By incorporating QC metrics into the Radiation Scorecard, radiation safety measures specific to the technology employed can become integrated into patient safety and provide an objective means to include technology (image display, acquisition, and processing devices) into the overall analysis of patient safety.

As previously mentioned, the medical physicist is an integral part of the multi-disciplinary consultation team. Their job is to create quality control (QC) and quality assurance (QA) programs that take into account quality and safety measures as it relates to the technology being used (both hardware and software). These measures can include the periodic determination of whether equipment used complies with industry and community-wide regulations for safety (i.e., radiation emissions, image quality), integration of phantoms into the modalities for calibration and recording of quality/radiation data, and identification of new technologies (e.g., CAD program specially designed for ultra low-dose CT acquisition parameters) that can further improve the quality/safety profile of the imaging provider and individual patient.

This in effect inserts the medical physicist into the comprehensive evaluation of technology, patient safety, quality measures, prospective data collection and analysis, and physician/patient consultation.

This data can in turn become an integral part of P4P initiatives, specifically as it relates to the technical component of medical imaging reimbursement.

G. Industry (Vendors)

By placing greater emphasis and accountability on radiation dose and patient safety, modality vendors and their products will also be held to a higher level of accountability. By making radiation dose profiles available to all stakeholders in the delivery of medical imaging services, technology selection and implementation will take into account radiation dose, detector efficiency, and image quality. By partially tying reimbursements to performance (P4P), a greater emphasis will be placed on safety-related concerns, which should in theory further drive new dose reduction technologies and applications.

At predefined time intervals set by the user or by default by the program 110, the individual Scorecards (patient, radiologist, clinician, physicist, and administrative) are automatically delivered by the program 110 to the respective parties by e-mail, facsimile, etc., in steps 609 and 705, for example. The program 110 provides the scorecards with trending analyses and highlighted areas of outliers (beyond two standard deviations of the mean) in each of the presented metrics (see U.S. patent application Ser. Nos. 11/699,349, 11/699,350, 11/699,344, 11/699,351, and 11/699,348). Each respective scorecard contains information for the stakeholder that outlines how each measured variable relates to the local, regional, and national counterparts (from data within the respective databases 113, 114). This information is in turn made available to the public and third party payers for P4P programs that tie radiation safety and image quality to reimbursement.

Since all patient-specific clinical and imaging data is recorded by the program 110 using a standardized format and stored within the centralized databases 113, 114 (see steps 309 and 627), all newly acquired Radiation Scorecard data is incorporated into the databases 113, 114, regardless of the exam location. The Radiation Scorecards are therefore portable, redundant, and easily accessible.

d. Radiation Databases

The resulting Radiation Scorecard databases 113, 114 can be used for a number of clinical applications pertaining to the individual patient's treatment of existing disease and preventive medicine. In addition, the data from a large number of individual patients' databases 113, 114 can be pooled for research purposes to determine new and improved ways to utilize radiation for medical diagnosis and treatment, determine the relationship between specific genetic traits and therapeutic response (relative to radiation), and correlating radiation carcinogenesis risks with genetic profiles.

In one example, an individual patient with newly diagnosed lung cancer undergoes a series of tests for diagnosis, staging, and treatment planning. During the course of the diagnostic work-up, the patient has chest radiographs, chest CT, and a nuclear medicine bone scan for staging resulting in a defined radiation exposure for each exam, which is recorded in the Radiation Scorecard database 113, 114 by the program 110 in step 626.

The patient also undergoes fluoroscopic biopsy of the lung tumor for diagnosis and the radiation exposure during this procedure is also recorded by the program 110 in step 626. The genetic markers for both the tumor and the individual patient are reviewed and cross-referenced by the program in step 634 with existing databases 113, 114 to determine the aggressiveness of the tumor, response to different types of treatment (e.g., chemotherapy, radiation therapy), and predilection of the patient to incur treatment-related complications (e.g., radiation fibrosis). By using the combined radiation-related genetic, historical, and clinical data; treatment planning can be optimized using the program 110 in step 202, as well as future screening studies (e.g., serial chest CT exams) scheduled and the data analyzed by the program 110 in step 634, to detect tumor recurrence.

In the case of follow-up chest CT exams in evaluating local tumor recurrence and/or metastatic disease, the cumulative whole body and organ-specific radiation exposure data can be used by the program 110 in step 619 (along with the specific clinical indication) to optimize the test selection, frequency of screening, protocol, and acquisition parameters. In this example, based on the cumulative radiation exposure to the involved lung (by both diagnostic and therapeutic radiation), and the patient's genetic profiles of both the patient and tumor, it is determined by the program 110 in step 619 that screening CT exams should be performed on a serial 6 month basis for the next 3 years.

Based on the specific clinical indication, patient profile (including their height/weight), and tumor aggressiveness; it is determined by the program 110 in step 619 that post-contrast imaging should be employed with specialized low-dose acquisition parameters, in conjunction with specialized image processing algorithms, and computer-assisted diagnosis (CAD) software. By carefully adjusting the acquisition parameters by the program 110 to the patient body habitus, clinical diagnosis, and reconstruction software by the program 110 in step 624, a net reduction of 40% radiation can be achieved without compromising diagnostic efficacy. By the program 110 combining meta-data from large patient populations in step 622, these individual Radiation Scorecard databases 113, 114 can facilitate improved screening, diagnosis, treatment planning, and overall patient safety.

e. Data Mining

Another important feature of the Radiation Scorecard of the present invention is the standardization of data elements contained within databases 113, 114, which provides a mechanism for large-scale data mining by the program 110. By creating uniformity in the manner in which radiation data (such as, exposure parameters utilized for acquisition (kilivoltage (kv) and milliamps (ma)), dose optimization techniques employed (e.g. real-time dose modulation, exposure time, acquisition speed, radiation exposure index value, subject-to-image distance (SID), subject-to-object distance (SOD), number of images acquired, image object description (IOD), exam type (imaging modality specifications), anatomic region, patient body habitus (height, weight, thickness), entrance surface dose (derived calculations), dose area product (derived calculations), critical organ dose (derived calculations), and type and quantity of pharmaceuticals administered (nuclear medicine)) is collected, stored, and analyzed by the program 110, these databases 113, 114 provide the means for comprehensive meta-analysis for large scale clinical outcomes studies, which to date are not available.

Once these standardized databases 113, 114 are created and individual data elements can be stratified, important cause and effect relationships can be established by the program 110, thereby creating an improved mechanism for "best practice" guidelines.

f. Radiation Scorecard Components

The present invention is a Radiation Scorecard including several different components, which individually record data for the user, relative to the patient's individual radiation history (i.e., diagnostic medical imaging performed, such as general radiation, mammography, CT, fluoroscopy, interventional fluorography, and angiography, and nuclear medicine); technical components of the exam performed (i.e., current exam type and dose calculation; specialized dose reduction techniques employed, radiation dose "savings" (comparison of current dose with reference dose), mean dose for alternative imaging exam (based on clinical indication), mean dose of alternative technology for same exam type (e.g., film/screen mammography), mean dose of local, regional, and national reference standards, itemized medical imaging and radiation dose history, cumulative lifetime radiation dose calculation, calculation of lifetime carcinogenesis risk, clinical profile (including current and past medical history); and QA ramifications (such as, exposure parameters utilized for acquisition (kilivoltage (kv) and milliamps (ma)), dose optimization techniques employed (e.g., real-time dose modulation, exposure time, acquisition speed, radiation exposure index value, subject-to-image distance (SID), subject-to-object distance (SOD), number of images acquired, image object description (IOD), exam type (imaging modality specifications), anatomic region, patient body habitus (height, weight, thickness), entrance surface dose (derived calculations), dose area product (derived calculations), critical organ dose (derived calculations), and type and quantity of pharmaceuticals administered (nuclear medicine)).

These data can be stored in a centralized database 113, 114, by the program 110, which can be accessed by the program 110 on local, regional, national, and international levels for comparative analyses.

The individual patient radiation history is intended to provide an educational tool for patients and referring clinicians, for the program 110 to track current and historical radiation exposures, and the relative risk of radiation-induced carcinogenesis. (This is a derived calculation using reference data from the medical literature correlated with the patient's lifetime radiation exposure.)

In addition for the program 110 to record the current and longitudinal dose measurements incurred to the patient, radiation "savings" will be calculated and reported by the program 110 in the Patient Radiation History Scorecard, by comparing radiation dose measurements associated with the current exam performed with a number of reference dose measurements.

These reference dose differential measurements are calculated by the program 110 in step 310, in several ways:

1) Savings between current exam with same exam type using standard technique. (e.g., low dose chest CT using 11 mas versus conventional chest CT using 180 mas).

2) Savings comparing current exam type with an alternative exam type, based on clinical indication. (e.g., digital subtraction radiography versus conventional chest CT for lung nodule detection).

3) Savings comparing current exam type/technology with alternative technology (same exam type) (e.g. digital mammography versus film/screen mammography).

4) Savings comparing current exam type and technique with reference database standards (local, regional, national) (e.g., current dose measurements for conventional chest CT compared with mean dose measurements from national radiation database (using similar technical parameters and patient profile)).

The technical components described above, are included in the Radiation Scorecard, and will include multiple exam and patient-specific data points used in the calculation of the radiation dose as described previously. Many of these data can be directly acquired from the DICOM (Digital Imaging and Communication in Medicine) header (which is intrinsic to all digital medical images), individual imaging modality, dose area product (DAP) meter, or radiology information system (RIS).

g. Quality Assurance and Dose Optimization

The concept of automating quality assurance (QA) and creating a comprehensive QA database (databases 113, 114) derived from objective QA metrics (tied to individual stakeholders) and is described in copending U.S. patent application Ser. No. 11/412,884. The information described therein can be directly integrated by the program 110 with the Radiation Scorecard to create a mechanism for synergistically monitoring and improving QA, while simultaneously providing radiation dose reduction. The derived radiation dose measurements are downloaded by the program 110 to the radiation database 113, 114 and included in the QA portion of the Radiation Scorecard.

The QA information is analyzed by the program 110 in step 631 and 632, to correlate radiation dose and image quality and provide valuable feedback to technologists, administrators, physicists, and radiologists as described above, in their combined quest to maximize radiation dose reduction and image quality. As new imaging technologies, applications, and techniques are introduced into clinical practice, this QA database becomes instrumental in providing educational feedback and assist with training.

The program 110 creates image quality standards and then adjusts image acquisition parameters for a given medical imaging exam, so that these image quality thresholds are not exceeded (see step 629). By doing so, QA standards are maintained prospectively (while being documented and continuously analyzed by the program 110), and the patient receives the "lowest possible" radiation dose for a given exam. The input data collected by the program 110 and analyzed to define these QA standards takes into account multiple factors including (but not limited to) the clinical indication, anatomic region, imaging modality, patient body habitus, patient medical history, technology utilized, and previous imaging data (in the forms of previous imaging exams, reports, and acquisition parameters). In addition, the program 110 can incorporate individual preferences of the interpreting radiologist or clinician (e.g., image processing, display parameters) to ensure that the individual "reader's" preferences are taken into account when determining optimal acquisition parameters.

One of the prerequisites required for this synergy is the integration of technology that allows the program 110 to objectively quantify image quality at the point of image capture. A number of existing technologies can provide this information, including peak signal to noise ratio (PSNR) and the just-noticeable-difference metric (JND). Both of these software programs can be integrated into existing technology at the level of the imaging modality to provide instantaneous feedback to the technologist at the time image acquisition parameters are input.

The program 110 optimizes exposure parameters and reduces radiation dose as follows:

In step 620, an initial ("QA Scout") image is obtained in the customary fashion, but using $\frac{1}{10}^{th}$ of the conventional dose by the program 110.

In step 621, this QA Scout image is then reviewed by the program 110 using an objective image quality measuring tool (PSNR or JND), which can quantify the amount of noise contained within the pixels of the Scout image.

The program 110 then performs a statistical analysis of noise contained within the ultra low dose acquisition image ($\frac{1}{20}^{th}$ of normal dose), and then automatically queries the comprehensive database 113, 114 in step 622 to determine optimum exposure parameters (i.e., radiation dose) based on a number of factors including (but not limited to):

a) Patient preferences (previously described)
b) Patient body habitus
c) Clinical indication
d) Pathology in question
e) Pre-defined threshold of image quality.

The database 113, 114 is also queried by the program 110 in step 622 to determine how other related technologies (e.g., CAD, specialized image processing algorithms) can be integrated into the process to further reduce image exposure parameters while maintaining the pre-defined image quality threshold.

The program 110 can also factor into the equation the performance of the individual radiologist or clinician who will be interpreting the imaging dataset. Based on the QA ad Radiation Scorecard data analysis, each individual "reader" will have a distinct profile as to their own diagnostic accuracy and performance for different degrees of radiation exposure. Some readers may have better performance than others at extremely low dose exposures. This data needs to be factored into the analysis when selecting "optimized" exposure parameters a priori (see steps 623 and 624). In addition, the patients will want to have this information when selecting the providers.

Another important application for the QA Scout is the ability of the program 110 to selectively deliver different exposure parameters to different areas of a single exam. For instance, if the exam performed is to re-examine a documented lung nodule, then the specific anatomic area of interest (and pathology) can be identified by the program 110 to insure maximum dose is delivered to that specific region, while lower exposure levels are delivered elsewhere. This in effect can decrease the cumulative radiation exposure without sacrificing the critical diagnostic information and diagnostic accuracy of interpretation.

The program 110 of the QA Scout can identify the area of concern and calculate differential exposure parameters in step 624 to ensure detectability of the area of interest, while maintaining lower (yet acceptable) quality parameters in the remaining portion of the imaging exam. If the program 110 was to use the JNDmetric as the visual discrimination model for quantification of image quality (see step 621), they could set the quality threshold of 1 JND (just noticeable difference) in the right upper lobe (where the nodule was previously detected) and set a separate quality threshold of 2 JND for the remaining areas. This data can then be longitudinally tracked by the program 110 (in conjunction with the QA Scorecard) to ensure that diagnostic accuracy is not compromised. By doing so, this becomes an iterative tool to balance the competing demands of optimizing image quality and radiation dose simultaneously.

In step 623, the program 110 then recommends the optimum exposure parameters by determining the lowest exposure parameters which maintain the desired threshold of image quality.

Note the desired level of image quality can sometimes vary, depending upon the clinical indication, and the desired level will be noted in the program 110.

In one example, a patient has had serial chest radiographic studies with documented pulmonary edema and now has a newly inserted central venous catheter. The current exam was performed to assess catheter placement. The image quality requirements for this exam are not as high as another radiographic exam (performed for the first time), on a patient with cough and suspected lung cancer. As a result, image quality requirements may vary according to a number of factors including (but not limited to) the modality, anatomic region being evaluated, clinical indication, past history, and historical imaging exams, which are determined by the program 110.

The above technique of the present invention will reduce the radiation exposure by 30-50% over conventional methods and improve overall image quality. The fractional dose of the "QA Scout" image is so low, that it would have a negligible impact on total dose.

The ability of the program 110 to dynamically query, retrieve, and analyze data from the Radiation Scorecard (and QA Scorecard) database 113, 114 prior to exam performance improves workflow, image quality, and dose reduction. As soon as the order for a given exam is approved by the clinician (using CPOE and Radiation Scorecard decision support), a query can be automatically generated by the program 110 that reviews a number of parameters including:

i) Patient imaging exam history (including prior exposure parameters and corresponding QA ratings)
ii) Patient medical history
iii) Clinical indication
iv) Body habitus (BMI)—available in both the RIS and EMR
v) Anatomic region
vi) Modality
vii) Technology Utilized.

The data obtained from this QA/radiation dose optimization process would be stored by the program 110 in the Radiation Scorecard and QA databases 113, 114, and be used in the future by the program 110 for decision support. The program 110 can use this data to perform the following:

i) Schedule follow-up exams on the same patient.

ii) Formulate a reference database for different patients (who fit the same or similar clinical profiles).

iii) Formulate a reference for development of software algorithms (e.g., image processing, CAD) to enhance the detection of pathology using ultra-low dose techniques.

iv) Formulate an identification of "disease specific" exposure parameters (e.g., pneumonia versus cancer versus trauma).

While this approach can be utilized for digital radiography and mammography, a modified strategy would be used for CT, which consists of multiple volumetric images (as opposed to a small finite number) within a single exam.

In another embodiment, instead of obtaining a conventional QA Scout image for anatomic localization, a series of ultra-low dose Scout images would be obtained which would create a cross-sectional (i.e., 3-dimensional) QA Scout image using the following steps.

Using the same technique (JND or PSNR), the program 110 determines the amount of noise within pixels of each individual CT QA Scout image.

The program 110 then determines, in step 621, the optimum exposure parameters to maintain a pre-determined quality threshold and achieve the lowest radiation dose possible.

The program 110 will adjust the exposure parameters according to the specific anatomic region being evaluated. For example, in an abdominal/pelvic CT, the optimized exposure parameters would be different when imaging through the liver as opposed to imaging through the bony pelvis, and the program 110 will adjust the parameters accordingly.

The combined imaging and QA/Radiation data is stored and analyzed by the program 110 so that it can be correlated with radiologist/clinician subjective perceptions of image quality to ensure that perceived quality is maintained. Due to differences in visual perception, education, and clinical experience; some radiologists or clinicians may be able to accommodate to a larger degree at increasing levels of noise within an image without compromising diagnostic accuracy. The individual reader performance and subjective perceptions (which are tracked in the Radiologist QA Scorecard) must be correlated with this Radiation Dose Optimization technology (above) to provide the required customization.

In addition, CAD algorithms will be refined by the program 110 to maximize performance using the ultra-low dose techniques of the present invention. By the program 110 correlating observer/CAD diagnostic accuracy with the EMR (part of the QA/Radiation Scorecard metrics), this allows for patients and third party payers to identify imaging provider performance, in terms of combined image quality, radiation dose reduction, and diagnostic accuracy. These data can become integrated into Pay for Performance (P4P) programs by the program 110, that provide economic incentive to those providers with documented performance measures exceeding pre-determined thresholds.

h. Technologists and Technique Optimization

It is important to note the significance of technology and the ability of the national database 113, 114 to assist with technique optimization.

There are two fundamentally different technologies utilized: computed radiography (CR) and direct radiography. Due to differences in detector efficiency, these technologies have different capabilities for dose reduction and must therefore employ different acquisition parameters. At the same time, DR systems have several different types of detectors, each of which has a different efficiency profile. As a result, technique optimization requires knowledge of the technology being utilized and cross-referencing this technology (and patient profile), with comparable technologies/patient profiles by the program. Other technology-related factors to consider include equipment manufacturer, software, and age.

The program 110 identifies a comparable exam and patient profile from an image quality/radiation dose optimized exam in the database 113, 114 (also, see Decision Support, below) in step 622. If a direct match is not found in the patient's own database 113, 114, then the query by the program 110 tries to identify a "match" from the local, regional, or national databases 113, 114. The technical parameters from this "optimized" exam would be integrated into the patient's imaging file by the program 110 (and stored at the levels of the imaging modality, RIS, and PACS), so that when the technologist prepares to begin the exam these default parameters are displayed by the program 110 in step 707. The various parameters identified by the program 110 would pertain to exposure, collimation, reconstruction and image processing algorithms. The technologist can proceed in one of three ways:

i) Use the default parameters.

ii) Over-ride the default parameters through manual input.

iii) Elect to use the aforementioned "QA Scout" technology to determine optimized parameters based on PSNR/JND analysis of the ultra-low dose scout image.

i. Sequential Dose Adjustment

The concept of sequential dose adjustment in a multi-image dataset is one component of the Radiation Scorecard and maximizes dose reduction without compromising diagnostic efficacy.

An illustrative example follows with respect to a spine radiographic series to evaluate scoliosis.

For this type of exam, the anatomic region of interest is the thoracolumbar spine, and the pathology in question is abnormal curvature. Other anatomic regions contained within the images (e.g., renal fossa) are "non-essential" and slight degradation in image quality can be accepted, provided the key diagnostic information attributable to the spine is present.

This concept of sequential dose adjustment also applies to serial images within a multi-image exam dataset (e.g., CT) or images that are performed in a temporal fashion for reassessment of previous pathology. An example of this would be an apical lordotic chest radiograph to evaluate a suspicious nodular density overlying the right apex, visualized on the conventional chest radiographic exam. The critical data contained within the follow-up image is localized to the right apex. Since the remaining lung fields have been recently evaluated by the clinician and radiologist and found to be normal, the technical requirements for the apical lordotic image focus on a small anatomic region (right apex), and may allow for lower exposure parameters (when compared with the original radiographic exam) to satisfactorily answer the clinical question at hand.

While QA responsibilities are largely attributed to technologists who acquire the imaging data at the modality, additional QA responsibilities reside within other stakeholders including administrators, radiologists, and clinicians as noted above. A portion of these QA responsibilities deal with ensuring that radiation dose optimization is maintained by utilizing appropriate technology (administrators) (see step 633), appropriate protocols (radiologists) (see step 705), and exam ordering (clinicians) (see step 601).

When the program 110 analyzes corresponding data from the QA and Radiation Scorecards to identify deficiencies in the metrics being tracked and analyzed (relative to community and national standards within the Scorecard databases 113, 114), feedback is immediately provided by the program 110 to the individuals involved. If patterns of continued poor performance are identified by the program 110, then remedial education is required and the individuals notified in steps 610, 706, and 631, for example, with the potential for removal of clinical/administrative privileges if the problem is not rectified (which can be automatic). The strength of this QA/Radiation tracking and analysis lies in the diversity and richness of data contained within these databases 113, 114. Trending analysis of this data by the program 110 provides an objective means to document compliance and quality improvement, in the event that outliers are identified by the program 110.

While a number of quantifiable metrics can be derived from the various data elements within the Radiation (and QA) Scorecard, one important data point for universal comparative analysis is the "Dose to Quality Index". The DQI is a defined as the ratio of radiation dose (as defined by the effective dose) divided by an objective image quality measure (as defined by PSNR or JNDmetric). This index provides a universal mechanism to compare a multitude of factors (e.g., different imaging providers, different types of technology, different patient populations) in radiation dose optimization and for the program 110 to correlate it with clinical outcome measures (e.g., interpretation accuracy). Note that this index can take into account both objective and subjective measures of image quality, with the subjective measures provided by radiologists and clinicians.

j. Decision Support

One of the most important benefits of the Radiation Scorecard is its ability to provide guidance to medical imaging multiple stakeholders in the various processes relating to exam optimization, such as: diagnostic medical imaging, institution/facility where exam is performed, technologist performing exam, ordering clinician, interpreting radiologist, room location, equipment specifications, type of exam, technique employed, clinical indication (relevant disease states and diagnoses), equipment quality control (QC) measurements and calibration, mean image quality (QA) score, and calculated dose area product.

With respect to the therapeutic medical data, the following is collated: therapeutic procedure performed, date, time, and duration of treatment, technology utilized, radiation source, incremental and cumulative radiation dose, physician performing procedure, critical organ doses, 3-dimensional anatomic reference map of radiation dose exposures, relevant medical/surgical data, side effects/complications of therapy, and list of medications.

In addition, with respect to non-medical radiation sources, the following is collated: source of exposure, energy profile, cumulative radiation dose, date, time, duration of exposure, geographic location during exposure, activity performed during exposure, critical organ doses, and dose area product. Finally, a genetic profile is collated, using: genetic (DNA) and proteinomic analysis, predisposition to disease states, prediction to radiation injury, and molecular imaging profile (diagnostic, therapeutic).

In an exemplary embodiment, as discussed above, at the point of exam order entry, the ordering clinician places an electronic order for a specific medical imaging exam in step 601, based on the patient's clinical presentation and the presumptive medical diagnosis. This electronic ordering process can be facilitated by the computerized physician order entry (CPOE) systems, where the program 110 provides educational feedback to the ordering physician to assist with exam selection. CPOE technology utilizes the clinical information provided to determine the single "best" medical imaging exam based on a series of appropriateness criteria (see step 602).

An exemplary case is where a family practice physician is evaluating a youngster for ankle trauma and suspected fracture. If the physician was to request a CT exam as the initial imaging exam, the program 110 of the CPOE system would instead advise digital radiography as the preliminary screening study based on statistical analysis of large patient populations presenting with similar symptoms and clinical findings.

The program 110 of the present invention thus, would take into account the "radiation" ramifications of these medical imaging studies, and will make recommendations for exam selection in step 606. Important factors are taken into account by the program 110 including the patient's pre-existing medical history, prior radiation exposure, and susceptibility to radiation injury, pediatrics, past history of therapeutic radiation, and those patients with genetic profiles placing them at greater risk to radiation-induced injury.

Using the patient-specific Radiation Scorecard data, established appropriateness criteria, and general comparative radiation dose schedules (i.e., average radiation dose associated with each type of medical imaging examination), the program 110 can cross-reference the clinical history and physical exam findings with these radiation data to provide objective data to the ordering clinician as to the "relative value' of different medical imaging exams for each particular patient (step 607). This relative value data can also take into account different exam protocok and allow the referring clinician to select the specific exam of choice after being presented comparative radiation data. To illustrate how the Radiation Scorecard would provide this decision support in order entry, three representative examples follow:

In the first exemplar, a pregnant patient (in her second trimester) with acute onset of shortness of breath and suspected pulmonary embolus (blood clot) presents. For this particular diagnosis, there are 3 exams commonly ordered which include a pulmonary angiogram (PA), CT angiography of the chest (CTA), and ventilation-perfusion lung scan (VQ).

The comparative whole body radiation doses (in milliSieverts [mSv]) associated with these imaging exams is as follows:

PA: 30 mSv
CTA: 5 mSv
VQ: 10 mSv

However, in light of the patient's age (26), excellent overall health, and lack of pre-existing medical history the concern for underlying lung disease is negligible. For this reason, the program 110 advises that if the VQ is selected, only the perfusion portion of the exam is required, thereby reducing the total dose to 5 mSv, which is the equivalent dose of the CTA.

Additional information obtained within the patient's EMR states the patient has a pre-existing history of contrast allergy, which effectively negates the CTA as a viable alternative. While not initially considered by the clinician, the program 110 also proposes the possibility of the bilateral lower extremity ultrasound in the assessment of deep venous thrombosis. If positive, this could effectively eliminate the need for the VQ scan and make the diagnosis without any radiation dose to the patient (and fetus).

In the second exemplar, an adolescent male (12 years old) with right flank pain and suspected urolithiasis (kidney stone) presents. For this particular diagnosis, there are 4 commonly performed imaging exams recommended by the program 110, including abdominal radiographs (XR), an intravenous pyelogram (IVP), abdominal/pelvic CT (CT), or abdominal ultrasound (US).

Because the patient in question is a pediatrics patient, radiation dose is of critical importance and should be an extremely high priority in the order decision-making process. Before ordering one of the more definitive exams (IVP, CT, or US); many physicians will first order an abdominal radiographic series (consisting of a single chest radiograph and 2 abdominal radiographs) for general assessment of abdominal pathology. In this particular case, the patient presents with no symptoms referable to the chest and very specific signs, symptoms, and relevant history of urolithiasis (i.e., flank pain radiating to the testis and hematuria, along with a past medical history of previously documented renal calculus).

When the program 110 compares the radiation dose exposures associated with each type of exam, the program 110 can assess that the single "best" exam (from a radiation dose perspective) is ultrasound, followed by CT and then IVP. The standard 3-view abdominal series would add approximately 0.15 rads, which, if the program 110 assesses to be important, could easily be reduced to 0.05 rads by selecting a single supine abdominal radiograph in lieu of the 3-view series.

When reviewing the patient's comprehensive Radiation Scorecard, a 6 mm right renal calculus was reported on an outside abdominal radiograph performed two weeks earlier. This was not available in the hospital PACS archive due to the fact it was performed outside of the host institution. When presented with this compilation of data, the clinician elected to go straight to ultrasound with the presumptive diagnosis of right renal calculus.

In the third exemplar, an elderly male (72 years old) with past medical history of lung cancer presenting with hemoptysis (coughing up blood). For this particular exam, there are 2 commonly performed exams including chest radiographs (XR) and chest CT (CT). For this particular patient, past medical/radiation history is of critical importance due to the fact that the patient had been previously treated with external radiation therapy for lung cancer, resulting in a cumulative exposure >100 rems. The Radiation Scorecard compiled by the program 110 also contains a detailed record of all subsequent radiation exposures, which include the most recent imaging studies consisting of a chest CT performed 2 months earlier, which reported no evidence of active (i.e., recurrent cancer) disease.

The standard chest radiographic series produces a radiation dose on the order of approximately 0.2 mSv, compared with 5 mSv for a standard chest CT. Due to the fact that the patient had a recently performed "conventional" chest CT, which was reportedly normal; a repeat "conventional" chest CT may not be required. Instead, the program 110 may recommend that an ultra-low dose CT be performed to address the clinical question at hand, and only have an associated radiation dose of 0.1 mSv (less than the standard chest radiograph). This ultra-low dose CT is determined by the program 110 to be efficacious when considering a number of factors including the patient's body habitus (6 feet tall, 140 lbs.), imaging history, presumptive diagnosis (pneumonia), available technology (64-channel CT scanner, specialized image processing algorithms to reduce noise).

In a similar manner to guiding clinician order entry, the Radiation Scorecard can also function to provide decision support to the technologist. Once the exam has been ordered and verified in step 611, the technologist (and radiologist) is tasked with determining the optimal acquisition parameters and protocol for the exam in question. Using the last example of the elderly patient with hemoptysis, the program 110 presents the option of employing a specialized protocol for the requested chest CT exam, thereby reducing the radiation dose from 5 mSv to 0.1 mSv (see steps 623-625)

In accordance with the recommendations for modifying exam and protocol selection, the program 110 would present optimized acquisition parameters to the technologist, along with recommendations for specialized image processing algorithms to assist with noise reduction. These recommendations would be derived by the program 110 from both the individual patient and national Radiation Scorecard databases 113, 114. Based on the patient clinical profile, body habitus, and technology being employed; the national Radiation Scorecard database 113, 114 could be queried to determine optimized image acquisition and processing parameters to use (see steps 623-625). These "recommended" acquisition parameters could subsequently be further optimized by performing a test scan and refining this test image for image quality using a visual discrimination model (e.g., JNDmetric) for image quality assessment. The specific methodology and invention for this technique is described above with respect to Quality Assurance.

Another important decision support application of the Radiation Scorecard (used for optimization of exposure parameters) is the integration of patient-specific body habitus data into exam acquisition. One of the challenges facing dose-reduction techniques is that of noise, which acts to limit image quality and decrease the conspicuity of pathology. As patients increase in size (especially girth), the amount of noise increases. This noise (and subsequent degradation in image quality) becomes exponentially magnified as lower exposure parameters (used to reduce radiation dose) are used.

The present invention simultaneously maximizes image quality and reduces radiation dose within acceptable levels to maintain diagnostic efficacy of the imaging exam. There are a number of ways the program 110 can be used to assist in this process.

The first is for the program 110 to query the database 113, 114 for exposure parameters used for the same exam type and patients of comparable size (height and weight), and cross reference this with the image quality ratings of those exams (QA Scorecard patent) (see step 618). Using this statistical approach, the program 110 would identify those comparable exams (e.g., low dose chest CT), performed on patients of similar body habitus, with the highest image quality ratings. From this list of database candidates, the program 110 would then identify those exams performed for similar clinical indications and on comparable technology. In the event that specialized software algorithms were utilized for image processing on these high quality exams, the program 110 could offer to provide these to the technologist (downloaded via the Internet) at the time of exam acquisition.

An alternative approach to the statistical model would be integration of body habitus measurements into the protocol and acquisition selection process by the program 110. Using a computerized model, the patient's body mass index (BMI) can be calculated by the program 110 by inputting the height (in inches) and weight (in pounds), along with a subjective measure of muscle mass. The program 110 can then derive optimized acquisition parameters based on a combination of the patient BMI, clinical indication, and exam type from the databases 113, 114.

These decision support applications of the Radiation Scorecard are aimed at assisting the clinician in exam selection and the technologist in exam optimization; with the ultimate goal of maximizing diagnostic efficacy while maintaining the highest level of patient safety through radiation dose reduction. Many other Radiation Scorecard deliverables can be derived by the program 110 from this data, which can assist the patient in selection of medical services. These would include periodic updates on radiation exposures, pre- and post-exam estimates (and the interventions used to maximize dose reductions), feedback on "dose savings" relative to reference standards for conventional techniques, and cumulative radiation carcinogenesis risk.

k. Training Programs

An additional feature of the Radiation Scorecard would be educational/training programs to assist different end-users (technologists, clinicians, administrators) and the patients in understanding the various factors that contribute to radiation and associated healthcare implications. Educational information can also take the form of quantitative predictions of radiation dose associated with a given procedure. These estimated exposure doses would take into account the anatomic region, modality, protocol employed, number of images, and acquisition parameters. By the program 110 providing this data "up front", both ordering clinicians and the patients can make educated decisions as to how differences in exam type or technology utilized could impact radiation dose exposure. These real-life quantitative measures will produce more highly educated consumers, reduce radiation exposure, and potentially stimulate new technology development.

1. Radiation Carcinogenesis

One of the well documented complications of ionizing radiation is radiation induced malignancy (carcinogenesis), which is directly proportional to the cumulative dose of radiation exposed over a patient's lifetime. While acute lethal doses of radiation can occur in the event of high dose exposure to radioactive substances (such as atomic or dirty bombs), the more common cause of radiation death is the result of carcinogenesis.

A number of factors can contribute to increased radiation exposure during a person's lifetime including the increased utilization of non-invasive medical imaging studies for diagnosis and disease prevention, increased patient life expectancy, development of new imaging techniques and applications (e.g., molecular imaging), and the increased use of radiation for therapeutic purposes. The advent of molecular imaging creates the unique possibility of diagnosing disease at the molecular level, which can further add to the cumulative radiation burden over the lifetime of a patient.

The program 110 that produces the Radiation Scorecard creates a mechanism to prospectively record, track, and analyze radiation exposure which can arise from medical applications, as well as environmental and occupational exposures. To date, these myriad of radiation sources are not uniformly tracked despite the well documented adverse effects of radiation.

Once radiation dose calculations are made by the program 110, the acquired data at the level of the imaging modality is simultaneously archived within multiple information technologies including the RIS, PACS, EMR. All pertinent data is downloaded into a comprehensive Radiation Scorecard database 113, 114 which can be stored at local, regional, national, and international levels. At any time, data can be accessed or added to by the patient or appropriately credentialed healthcare professionals through biometrics authentication.

The Radiation Scorecard data is in turn correlated with the individual patient's genetic profile and medical record by the program 110 to determine their underlying risk factors for disease occurrence and morbidity/mortality. As a new medical diagnosis is determined, the genetic profile can be used to predict disease expression. In addition, the Radiation Scorecard database 113, 114 can be queried and analyzed to predict the radiation exposure one would expect for that newly diagnosed disease (based on existing patterns of utilization for screening, diagnosis, and treatment planning) within the designated patient profile.

In one example, a patient has newly diagnosed lung cancer. Based on the patient's genetic profile and tumor staging (including DNA analysis), an estimate of future radiation exposure (both organ specific and whole body) for this new diagnosis is made based on expected use of medical imaging studies for diagnosis, treatment planning, and surveillance; along with any potential use of radiation for therapy. These disease-specific radiation estimates are continuously updated by the program 110 in accordance with changes in medical/imaging practice, the patient's specific disease state, and new technology developments.

As the cumulative radiation dose estimates are updated by the program 110, new trending analysis is provided by the program 110 to the patient and all designated healthcare providers, along with a calculated carcinogenesis risk based on actuarial analysis. The accuracy of these carcinogenesis measures would improve over time, as more accurate radiation data and outcomes analysis is realized, which is one benefit of the Radiation Scorecard.

If a "higher than expected" cumulative dose is calculated by the program 110, an emergent notification (with receipt confirmation) would be sent to the healthcare providers by the program 110, along with recommendations for suggested mechanisms to reduce future radiation dose. This could take a number of different forms including alternative diagnostic testing, decreased frequency of serial exams, or more aggressive use of dose-reduction imaging strategies.

In the same manner that medical-related radiation dose is tracked and analyzed, environmental and occupational exposures are also carefully monitored by the program 110, with automated alerts being automatically sent in the event that critical thresholds are realized (see steps 629-630).

EXAMPLE

In one exemplary embodiment, the following steps are taken in preparing the Radiation Scorecard.

In step 601, the physician places an order for a medical imaging exam using the PACS or RIS or other physician-related apparatus. In step 602, the Radiation Scorecard program 110 will query the Radiation Scorecard Database 113, 114 to determine the exam appropriateness based on the patient's medical history etc.

In step 603, the program 110 will query the database 113, 114 to determine if comparable imaging data is already present in order to provide a comparison of the type of imaging quality and results should be received.

In step 604, the program 110 will review the data on the patient, and their scorecard, to calculate the additional radiation burden from the proposed imaging study. This information will be compared by the program in step 605, against a maximum exposure amount that is considered safe for the patient, and the results provided to the clinician in step 606 with recommendations for exam type, protocol, and required interventions using decision support.

In step 607, the program 110 will provide information on technology options to minimize dose exposure to the patient.

In step 608, the program 110 will compile a radiation scorecard for the clinician based on the proposed imaging study, taking into account the patient's scorecard for forwarding and review by administrators, and for clinician review in step 609. Thus, the clinician's overall compliance and contribution to dose reduction will be assessed by the administrators, and by the program 110 against a database 113, 114 of other clinician scorecards.

In step 610, the program 110 will provide educational feedback to the clinician (as needed), based on the results of the clinician's scorecard. When educational steps are taken to reduce scorecard issues, the program 110 will take them into account and amend the clinician's scorecard to reflect the positive changes.

In step 611, if the patient's scorecard is not exceeded with respect to radiation dose etc., the exam confirmation is sent to the patient by the program 110 by electronic means (i.e., facsimile, e-mail etc.). The exam confirmation may include optimized exam data, which includes recommendations for dose reduction (based on individual patient and national database analysis from the program 110 query in steps 603 and 605, for example).

In steps 306-309, the program 110 will estimate the radiation dose of the ordered exam and potential alternative studies, and perform a historical review of cumulative dose exposure, and retrieve any associated educational data, and include them in the Radiation Scorecard for clinician, radiologist, technologist, and patient review.

In step 612, when the patient arrives for the exam, he/she will undergo a biometrics exam for authentication and identification, given by the technologist. If the biometrics is authenticated, and the patient identified, the program 110 will retrieve the patient-specific Radiation Scorecard from the patient-specific database 113, 114 in step 613.

In step 614, the program 110 will display the ordered exam specifics and radiation dose data, and the radiologist and clinician will approve the ordered exam and predicted radiation dose.

The technologist will prepare the patient for the exam, and in step 615, the program 110 will receive the biometrics from the patient at modality for authentication and access to the Radiation Scorecard database.

Once authenticated, the program 110 will display the exam profile (exam type, anatomic region, clinical indication, ordering clinician) in step 616, for technologist review and radiologist consultation if needed.

In step 617, the program 110 will submit an automated query of the Radiation Scorecard database 113, 114 to retrieve patient-specific radiation data, prior exam history, body mass index (BMI), and historic exposure parameters and image quality scores from the national Radiation Scorecard database 113, 114, to obtain comparable data from similar patient and technology profiles in step 618. Variables include: clinical indication, anatomic region, modality, patient body habitus (BMI), documented pathology, past medical history, genetic profile (DNA analysis), technology utilized.

In step 619, the program 110 will determine the optimized exposure parameters and corresponding radiation dose calculations, and identify supporting technologies to enhance dose reduction (e.g., specialized image processing, use of grids/filters), and display the same for the technologist review.

In step 620, the QA Scout of the program 110 obtains an ultra-low dose scout image obtained (at multiple levels for CT), and in step 621, correlates the scout image with the visual discrimination model (e.g., JNDmetric) to quantify the amount and location of the noise, and calculate the exposure parameters based on noise and predefined image quality threshold.

In step 622, the program 110 queries the Radiation Scorecard database 113, 114 to cross-reference comparable QA Scout data from similar exam types, patient profiles, and technology profiles.

In step 623, the program 110 generates options for maximized dose reduction based on selective anatomic regions/pathology of interest, for the radiologist to review and to provide assistance with optimization of the protocol and exposure parameters (ensuring image quality threshold maintained).

In step 624, the program queries the Radiation Scorecard database 113, 114 and performs the analysis to select the optimized exposure parameters. This analysis includes a QA Scout quantitative analysis of the image, and will include radiologist/technologist input.

In step 625, the technologist inputs the exposure parameters with links to the Radiation Scorecard database 113, 114, and conducts the exam.

In step 626, the exam is acquired and the data collected, and automated calculations of the organ specific dose, effective dose, and comparative dose calculations (prior comparable exams, alternate technologies, conventional techniques) are performed by the program 110, and stored in radiation databases 113, 114 in step 627.

In step 628, the exposure parameters that are recorded are transferred to the DICOM header, along with all pertinent data (patient profile, technology profile, exposure parameters, dose calculations, etc.), which is also transferred to multiple Radiation Scorecard databases 113, 114.

The Patient-specific Radiation Scorecard database 113, 114 is then updated by the program 110 to reflect the current exam. If any predefined thresholds are realized (relative to deficiencies in technology, protocol, acquisition parameters), automated alerts are sent to the respective parties (patient, referring clinician, radiologist administrator) by the program 110 in step 629.

If the critical threshold is realized (determined by genetic profile of patient, single and cumulative radiation dose exposures, and underlying medical condition of patient), emergent notification is sent by the program 110 in step 630 to a multi-disciplinary Radiation Consultation Team (consisting of medical physicist, IT specialist, technologist, radiologist, administrator, primary care physician). The Radiation Consultation Team serves as a patient advocate to ensure compliance to community-wide standards and make recommendations for required intervention to improve radiation safety. It also serves to ensure physician, radiologist, and technologist performance meets accepted standards.

Although the above steps relate to an imaging study, the sources of radiation exposure data could be provided by external (or implantable) sensors which monitor a patient's radiation exposure.

When the program 110 forwards automated alerts according to pre-defined templates, to the different stakeholders as in step 630, the data collected in the database 113, 114 is analyzed and the data used to guide education and training, new technology implementation, resource allocation, and creation of radiation standards in step 631.

Individual stakeholders and specific feedback provided include: Medical; Physicist: Technology QA/QC metrics, Quality/Dose Indices, Occupational/Environmental Exposures; Administrator: Technologist performance, Patient safety, Medico-legal risk, Departmental compliance; Radiologist: Comparative radiation data (based on local, regional, and national data), Supporting Technologies, Clinician compliance; Clinician: Radiation CME, CPOE compliance, Peer to peer comparative data; IT Specialist: Database integrity, technology integration, data security; and patient: Cumulative dose exposure, Carcinogenesis risk, Educational Programs.

The program 110 provides the above feedback to each of the stakeholders in step 31 to improve quality assurance.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of providing a radiation scorecard for controlling radiation dose exposure to an individual comprising:
    calculating, using a processor of a computer system, an entrance skin dose and effective dose to a patient, for a predetermined medical procedure;
    calculating, using said processor, an area of irradiation to said patient;
    calculating, using said processor, an effective radiation dose to said patient using a radiation detector, for said medical procedure, as a summation of a product of an entrance skin dose times fractional organ doses stored in a database, times critical organ dose weighting factors retrieved from said database, wherein said medical procedure is an imaging examination using an imaging device;
    storing said effective dose for said patient, in said database;
    deriving, using said processor, a cumulative radiation dose for said patient which is compared against a maximum radiation exposure amount safe for said patient;
    calculating, using said computer, said radiation dose exposure from said comparison, to result in optimized radiation dose exposure parameters for said patient;
    deriving a patient radiation scorecard including said cumulative radiation dose, said maximum radiation exposure amount, and said optimized radiation dose exposure parameters, and storing said patient radiation scorecard in said database;
    retrieving comparable data to an examination profile, which contains patient data retrieved from said database on said patient, on said radiation dose exposure from said database;
    comparing said comparable data to said patient data on said radiation dose exposure from said imaging examination profile;
    displaying said optimized radiation dose exposure parameters and corresponding radiation dose exposure calculations derived from said comparison using said processor, on a display; and
    identifying technology options including alternative imaging examinations or alternative examination protocols, to minimize said radiation dose exposure to said individual patient.

2. The method of claim 1, further comprising:
    compiling, using said processor, one of a clinician, radiologist, administrator, or technologist scorecard based on compliance with at least said minimization in said radiation dose exposure.

3. The method of claim 1, further comprising:
    automatically calculating, using said processor, an organ specific dose, effective dose, and comparative dose for said patient prior to said imaging examination.

4. The method of claim 1, further comprising:
    forwarding automated alerts to a plurality of parties when predefined thresholds are reached relative to deficiencies in at least one of technology, protocol, or acquisition parameters.

5. The method of claim 1, further comprising:
    receiving the examination order for said imaging examination; displaying the imaging examination profile on a display of a computer system, said imaging study exam examination profile which contains the patient data retrieved from a said database on the individual said patient;
    retrieving said patient radiation scorecard from said database;
    compiling a clinician radiation scorecard, using said processor, which includes at least said optimized radiation dose exposure parameters, and said technology options to minimize said radiation dose exposure.

6. The method of claim 5, further comprising:
    obtaining an ultra-low dose image during said imaging examination using said imaging device;
    correlating, using said processor, said ultra-low dose image with a visual discrimination model to determine said radiation dose exposure parameters;
    cross-referencing, using said processor, said radiation dose exposure parameters with radiation data in said database of said computer system, to obtain comparable data;
    displaying options on a display of said computer system to maximize radiation dose exposure reduction based on said comparable data;
    selecting, using said processor, optimum radiation dose exposure parameters for said patient based on said maximized radiation dose exposure reduction; and
    inputting said optimum radiation dose exposure parameters into said imaging device.

7. The method of claim 6, wherein said correlation of said ultra-dose image with said visual discrimination model is to quantify an amount and location of noise in said image; and
    wherein said radiation dose exposure is calculated based on said amount of said noise and a predefined image quality threshold.

8. The method of claim 6, further comprising:
    performing, using said processor, an image analysis on an image obtained during said imaging examination using said imaging device;
    storing said image and said image analysis in a quality assurance database of said computer system;
    correlating, using said processor, said image and said image analysis with quality data on images stored in said database;
    creating an image quality score of said image, using said processor, based on said correlation; and
    using the highest image quality scores as technical defaults for a subsequent imaging examination, using said processor.

9. The method of claim 8, further comprising:
    informing a user by electronic means, that education or training is required when said image quality score is below a predetermined threshold.

10. The method of claim 9, further comprising:
    forwarding automated alerts to users when said image quality score is below another predetermined threshold.

11. The method of claim 8, wherein said radiation detector includes computed radiography or direct radiography devices.

12. The method of claim 8, wherein an entrance skin dose is calculated using said processor, by utilizing information from a calibrated dose area product (DAP) device installed on said imaging device or a point dosimeter.

13. The method of claim 8, wherein said entrance skin dose and said effective dose are calculated using said processor, using information from an point air-ionization chamber measuring air-kerma within a calibration dose area product (DAP) device.

14. The method of claim 8, wherein said entrance skin dose is calculated using said processor, using screen-film speed information from said imaging device, or radiation exposure index values provided by digital radiography systems in conjunction with reference values estimated by said processor for an imaging examination.

15. The method of claim 1, further comprising:
calculating said effective dose in mammography, using said processor, as a summation of individually calculated effective dose estimates for each imaging examination performed on said individual.

16. The method of claim 8, further comprising:
calculating, using said processor, said radiation dose exposure in computed tomography, using indirect measurements from plastic phantoms and stored in said database.

17. The method of claim 8, wherein said radiation dose exposure in nuclear medicine is provided from said database which includes data on a type and dose of radiopharmaceutical utilized.

18. The method of claim 8, wherein said imaging examination comprises:
collecting data from a radiation source during said imaging examination, using said imaging device;
transferring said data obtained from said radiation source to said database using said processor, and cross-referencing said data with a medical history on said individual, using said processor, to create a time-stamped radiation profile of said patient.

19. The method of claim 18, wherein said comparison of said radiation dose exposure against said maximum radiation exposure amount stored in said database, performed by said processor, is for a predetermined anatomic region/critical organ.

20. The method of claim 18, wherein said data from said radiation source is stored in a centralized local, regional, or national database.

21. The method of claim 18, wherein said radiation source includes external radiation data monitoring sources imbedded within said imaging device or said therapeutic device, or is attached to the patient.

22. The method of claim 18, wherein said radiation data monitoring source is connected to a biometrics device which establishes an identity of the patient, and which ensures proper linkage between data on said radiation dose exposure and said medical history stored on said patient.

23. The method of claim 18, further comprising:
storing data from said radiation data monitoring source, including a date and a time of exposure, a duration of radiation exposure, an amount of radiation dose, a geographic location of said patient, an anatomic area of exposure, an energy profile of said radiation dose exposure, and a geographic location of said radiation dose exposure to said patient during a predetermined time interval, in said database.

24. The method of claim 18, further comprising:
creating a real-time, temporal, topographical three dimensional anatomic map, using said processor, said map which illustrates an epicenter of said maximum exposure and a relative decay in said radiation dose exposure from said epicenter, that depicts said radiation dose exposure over time for said patient.

25. The method of claim 8, further comprising:
recording an environmental radiation dose exposure and an occupational radiation dose exposure and storing said environmental and occupational radiation dose exposures in Said database for analysis.

26. The method of claim 25, further comprising:
determining a directionality of radiation dose exposure using said processor, to establish and correlate said radiation dose exposure with environmental factors, to determine an extent and a direction of contamination to identify patients requiring emergent medical care and prophylaxis.

27. The method of claim 8, further comprising:
periodically analyzing examination orders by said clinician, and said corresponding radiation dose exposure to said patient, using said processor; and
comparing said analysis, using said processor, to other clinicians to include in said clinician scorecard.

28. The method of claim 27, further comprising:
notifying said clinician of required remedial education and training when said analysis shows an effect on patient safety or diagnostic efficacy.

29. The method of claim 9, wherein said user is a radiologist.

30. The method of claim 9, wherein said user is a technologist.

31. The method of claim 30, wherein said technologist analyzes productivity, image quality, retake/reject statistics, radiation dose exposure parameters, type of image processing utilized, and patient adverse outcomes.

32. The method of claim 8, wherein said administrator scorecard includes analysis, using said processor, of performance and adherence of clinicians, technologists, radiologists, departments, and technologies utilized, as well as technology selection and integration, to local, regional, national, and international standards.

33. The method of claim 32, further comprising:
creating a customized patient profile, using said processor, including all radiation dose exposures on said patient and potential alternative examinations, and a historical review of said cumulative radiation dose exposure, all of which is used to determine future medical decisions, including screening and preventative measures, consultative services, and provide direct feedback and educational programs to the patient.

34. The method of claim 8, further comprising:
incorporating quality control metrics on said radiation detector and compliance with industry and community safety standards, into said radiation scorecard, using said processor, to determine radiation safety measures specific to said radiation detector which are utilized.

35. The method of claim 2, further comprising:
periodically delivering said radiation scorecards, using electronic means, to said clinician, radiologist, administrator and technologist, said scorecards including trending analyses and comparisons with local, regional, and national counterparts.

36. The method of claim 8, further comprising:
storing in said patient radiation scorecard in said database, said medical history and radiation history of said patient, technical components of said imaging examination performed, specialized radiation dose exposure reduction techniques employed, radiation dose savings, mean radiation dose for alternative and same type imaging studies, mean radiation dose in local, regional, and national reference standards, itemized imaging examination and radiation dose exposure history, cumulative lifetime radiation dose exposure calculations, calculation of lifetime carcinogenesis risk, clinical profile of said patient, and quality assurance ramifications of said imaging examination to said patient.

37. The method of claim 8, further comprising:
receiving and storing adjustments to image acquisition parameters of said imaging device which performs said imaging examination on said patient, such that image quality thresholds are not exceeded and said patient receives only the minimum radiation dose exposure required for said imaging examination.

38. The method of claim 8, further comprising:
selectively providing different radiation dose exposure parameters derived by said processor, to different areas of a body of a patient during said imaging examination.

39. The method of claim 38, further comprising:
identifying an area of concern using said processor, and calculating differential radiation dose exposure parameters using said processor, to ensure detectability of said area of concern, while maintaining relatively lower but acceptable quality parameters in a remaining portion of said imaging examination.

40. The method of claim 7, further comprising:
obtaining said ultra-low dose image in a series of images from said imaging device to said computer system, such that a cross-sectional image is obtained and stored in said database;
determining an amount of said noise in pixels of each of said images using said processor; and
determining said optimum radiation dose exposure parameters using said processor, to maintain a predetermined quality threshold.

41. The method of claim 40, wherein sequential dose adjustment is used.

42. The method of claim 5, further comprising:
recommending selected imaging examination profiles, using said processor, based on said patient's medical history, prior radiation dose exposure, appropriateness criteria, susceptibility to radiation injury, pediatrics, past history of therapeutic radiation, and genetic profiles with risk.

43. The method of claim 5, wherein said comparable data includes data on patients of a same imaging study exam profile, and comparable size.

44. The method of claim 37, wherein said optimum acquisition parameters are based on a patient's body mass index, clinical indication, and imaging study exam type.

45. The method of claim 5, further comprising:
using said processor to query said database to determine an appropriateness of said imaging examination based on said medical history of said patient.

46. A computer system which provides a radiation scorecard for controlling radiation dose exposure to an individual, comprising:
a radiation detector, including an imaging device or a therapeutic device, for detecting radiation dose exposure on an individual;
at least one memory containing at least one program comprising the steps of:
calculating, using a processor of the computer system, an entrance skin dose and effective dose to a patient, for a predetermined medical procedure;
calculating, using said processor, an area of irradiation to said patient;
calculating, using said processor, an effective radiation dose to said patient using a radiation detector, for said medical procedure, as a summation of a product of an entrance skin dose times fractional organ doses stored in a database, times critical organ dose weighting factors retrieved from said database, wherein said medical procedure is an imaging examination using an imaging device;
storing said effective dose for said patient, in said database;
deriving, using said processor, a cumulative radiation dose for said patient which is compared against a maximum radiation exposure amount safe for said patient;
calculating, using said computer, said radiation dose exposure from said comparison, to result in optimized radiation dose exposure parameters for said patient;
deriving a patient radiation scorecard including said cumulative radiation dose, said maximum radiation exposure amount, and said optimized radiation dose exposure parameters, and storing said patient radiation scorecard in said database;
retrieving comparable data to an examination profile which contains patient data retrieved from said database on said patient on said radiation dose exposure from said database;
comparing said comparable data to said patient data on said radiation dose exposure from said imaging examination profile;
displaying said optimized radiation dose exposure parameters and corresponding radiation dose exposure calculations derived from said comparison using said processor, on a display;
identifying technology options including alternative imaging examinations or alternative examination protocols, to minimize said radiation dose exposure to said individual patient; and
the processor configured to execute the program.

47. A non-transitory computer readable medium whose contents cause a computer system to execute instructions of a program, the program comprising the steps of:
calculating, using a processor of the computer system, an entrance skin dose and effective dose to a patient, for a predetermined medical procedure;
calculating, using said processor, an area of irradiation to said patient;
calculating, using said processor, an effective radiation dose to said patient using a radiation detector, for said medical procedure, as a summation of a product of an entrance skin dose times fractional organ doses stored in a database, times critical organ dose weighting factors retrieved from said database, wherein said medical procedure is an imaging examination using an imaging device;
storing said effective dose for said patient, in said database;
deriving, using said processor, a cumulative radiation dose for said patient which is compared against a maximum radiation exposure amount safe for said patient;
calculating, using said computer, said radiation dose exposure from said comparison, to result in optimized radiation dose exposure parameters for said patient;
deriving a patient radiation scorecard including said cumulative radiation dose, said maximum radiation exposure amount, and said optimized radiation dose exposure parameters, and storing said patient radiation scorecard in said database;

retrieving comparable data to an examination profile, which contains patient data retrieved from said database on said patient, on said radiation dose exposure from said database;
comparing said comparable data to said patient data on said radiation dose exposure from said imaging examination profile;
displaying said optimized radiation dose exposure parameters and corresponding radiation dose exposure calculations derived from said comparison using said processor, on a display; and
identifying technology options including alternative imaging examinations or alternative examination protocols, to minimize said radiation dose exposure to said individual patient.

* * * * *